US006506595B2

(12) United States Patent
Sato et al.

(10) Patent No.: US 6,506,595 B2
(45) Date of Patent: *Jan. 14, 2003

(54) DNAS ENCODING NEW FUSION PROTEINS AND PROCESSES FOR PREPARING USEFUL POLYPEPTIDES THROUGH EXPRESSION OF THE DNAS

(75) Inventors: Seiji Sato, Ibaraki (JP); Naohiko Higashikuni, Ibaraki (JP); Toshiyuki Kudo, Ibaraki (JP); Masaaki Kondo, Ibaraki (JP)

(73) Assignees: Itoham Foods Inc., Kobe (JP); Shigeo Udaka, Nagoya (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/280,030

(22) Filed: Mar. 26, 1999

(65) Prior Publication Data

US 2001/0021515 A1 Sep. 13, 2001

(30) Foreign Application Priority Data

Mar. 31, 1998 (JP) ............................................. 10-087339

(51) Int. Cl.$^7$ ........................ C12N 15/00; C12N 15/09; C12N 5/00; C07H 21/04
(52) U.S. Cl. ................... 435/320.1; 435/325; 536/23.5; 536/23.51; 536/24.1; 536/24.2
(58) Field of Search .............................. 435/69.1, 71.1, 435/320.1, 325; 536/23.5, 23.51, 24.1, 24.2

(56) References Cited

U.S. PATENT DOCUMENTS

| 5,459,065 A | * | 10/1995 | Aust et al. |
| 5,686,418 A | * | 11/1997 | Culler |

FOREIGN PATENT DOCUMENTS

| CA | 2008824 C | * | 8/1997 |
| EP | 0177343 | | 4/1986 |
| EP | 0409113 A1 | * | 1/1991 |
| EP | 0790305 A1 | * | 8/1997 |
| JP | 3251185 A | | 11/1991 |
| JP | 06038741 A | | 2/1994 |
| JP | 06253862 A | | 9/1994 |
| JP | 07051072 A | | 2/1995 |
| WO | WO 93/17098 A1 | * | 9/1993 |
| WO | 9418331 | | 8/1994 |
| WO | 9640943 | | 12/1996 |

OTHER PUBLICATIONS

Udaka et al Methods Enzymol 217:23–33, 1993.*
Inoue et al ApplMicrobiol Biotechnol 48 (4):487–92, 1997.*
Chang et al Biochem J 329:631–5, Feb. 1998.*
Kato, Masashi, et al. "Efficient production of Casoxin D, a Bradykinin Agonist peptide derived from Human Casein, by *Bacillus brevis*", Bioscience Biotechnology and Biochemistry vol. 59, No. 11 (1995) pp. 2056–2059.
Takao M, et al. "Production of swine pepsinogen by protein–producing *Bacillus brevis* carrying swine pepsinogen complementary DNA", Applied Microbiology and Biotechnology vol. 30, No. 1 (1989) pp. 75–80.
Polayes D., et al. "Efficient cleavage of affinity tags from expressed proteins by TEV protease, recombinant", Protein Engineering vol. 8 (Suppl 1995) p. 89.
Yoshikawa, Kazumasa, et al. "Recombinant human glucagon: Large–scale purification and biochemical characterization", Journal of Protein Chemistry vol. 11, No. 5 (1992) pp. 517–525.
Muttilainen, Susanna, et al. "Heterologous production of the P1 porin of Neisseria meningitidis in *Bacillus subtilis*: The effect of an N–terminal extension on the presentation of native–like epitopes" Microbial Pathogenesis vol. 18, No. 5 (1995) pp. 365–371.
English translation of Abstract for Japanese Patent Application No. 06038741A.
English translation of Abstract for Japanese Patent Application No. 3251185A.
English translation of Abstract for Japanese Patent Application No. 07051072A.
English translation of Abstract for Japanese Patent Application No. 06253862A.

* cited by examiner

*Primary Examiner*—Mark Navarro
(74) *Attorney, Agent, or Firm*—Davidson, Davidson & Kappel, LLP

(57) ABSTRACT

This invention relates to a DNA comprising a nucleotide sequence encoding a fusion protein, wherein the fusion protein comprises: a sequence of signal peptide for Bacillus cell wall protein (CWP); a tag sequence for separation and purification of the fusion protein; a linker sequence; a sequence for chemical or enzymatic cleavage; and an exogenous polypeptide sequence, the sequences being linked in order, the signal peptide, tag and linker being optional sequences; and wherein the nucleotide sequence encoding a fusion protein is ligated to 3'-end of a nucleic acid sequence comprising a Bacillus promoter region; to a vector comprising the DNA; to a bacterium belonging to the genus Bacillus comprising the vector; and to a process for preparation of a useful polypeptide by culture of the bacterium.

24 Claims, 22 Drawing Sheets

FIG. 1

MWPsp-MWPmp10-(His)₆-Linker-Met-Proinsulin

```
  1 GTC GTT AAC AGT GTA TTG GCT AGT GCA CTC GCA CTT ACT GTT GCT CCA
    Val Val Asn Ser Val Leu Ala Ser Ala Leu Ala Leu Thr Val Ala Pro
                                    10

49 ATG GCT TTC GCA GCA GAA GAA GCA GCA ACT ACT ACA GCT CCA CAT CAT
    Met Ala Phe Ala Ala Glu Glu Ala Ala Thr Thr Thr Ala Pro His His
                20                                          30

97 CAT CAT CAT CAC GGT TCT CCA GTA CCT TCT GGA ATG TTT GTG AAC CAA
    His His His His Gly Ser Pro Val Pro Ser Gly Met Phe Val Asn Gln
                                    40

145 CAC CTG TGC GGC TCA CAC CTG GTG GAA GCT CTC TAC CTA GTG TGC GGG
    His Leu Cys Gly Ser His Leu Val Glu Ala Leu Tyr Leu Val Cys Gly
        50                                          60

193 GAA AGA GGC TTC TTC TAC ACA CCC AAG ACC CGC CGG GAG GCA GAG GAC
    Glu Arg Gly Phe Phe Tyr Thr Pro Lys Thr Arg Arg Glu Ala Glu Asp
                            70                                  80

241 CTG CAG GTG GGG CAG GTG GAG CTG GGC GGG GGC CCT GGT GCA GGC AGC
    Leu Gln Val Gly Gln Val Glu Leu Gly Gly Gly Pro Gly Ala Gly Ser
                                            90

289 CTG CAG CCC TTG GCC CTG GAG GGG TCC CTG CAG AAG CGT GGC ATT GTG
    Leu Gln Pro Leu Ala Leu Glu Gly Ser Leu Gln Lys Arg Gly Ile Val
                    100                                     110

337 GAA CAA TGC TGT ACC AGC ATC TGC TCC CTC TAC CAG CTG GAG AAC TAC
    Glu Gln Cys Cys Thr Ser Ile Cys Ser Leu Tyr Gln Leu Glu Asn Tyr
                                120

385 TGC AAC TAG
    Cys Asn ***
        130
```

FIG. 2

MWPsp-MWPmp10-Met-Proinsulin

```
  1 GTC GTT AAC AGT GTA TTG GCT AGT GCA CTC GCA CTT ACT GTT GCT CCA
    Val Val Asn Ser Val Leu Ala Ser Ala Leu Ala Leu Thr Val Ala Pro
                                     10

49 ATG GCT TTC GCA GCA GAA GAA GCA GCA ACT ACT ACA GCT CCA ATG TTT
    Met Ala Phe Ala Ala Glu Glu Ala Ala Thr Thr Thr Ala Pro Met Phe
                    20                                  30

97 GTG AAC CAA CAC CTG TGC GGC TCA CAC CTG GTG GAA GCT CTC TAC CTA
    Val Asn Gln His Leu Cys Gly Ser His Leu Val Glu Ala Leu Tyr Leu
                                40

145 GTG TGC GGG GAA AGA GGC TTC TTC TAC ACA CCC AAG ACC CGC CGG GAG
    Val Cys Gly Glu Arg Gly Phe Phe Tyr Thr Pro Lys Thr Arg Arg Glu
        50                                  60

193 GCA GAG GAC CTG CAG GTG GGG CAG GTG GAG CTG GGC GGG GGC CCT GGT
    Ala Glu Asp Leu Gln Val Gly Gln Val Glu Leu Gly Gly Gly Pro Gly
                        70                                      80

241 GCA GGC AGC CTG CAG CCC TTG GCC CTG GAG GGG TCC CTG CAG AAG CGT
    Ala Gly Ser Leu Gln Pro Leu Ala Leu Glu Gly Ser Leu Gln Lys Arg
                                        90

289 GGC ATT GTG GAA CAA TGC TGT ACC AGC ATC TGC TCC CTC TAC CAG CTG
    Gly Ile Val Glu Gln Cys Cys Thr Ser Ile Cys Ser Leu Tyr Gln Leu
                    100                                 110

337 GAG AAC TAC TGC AAC TAG
    Glu Asn Tyr Cys Asn ***
```

FIG. 3

MWPsp-MWPmp20-(His)₆-EGF-TEV-Somatostatin 28

```
  1 GTC GTT AAC AGT GTA TTG GCT AGT GCA CTC GCA CTT ACT GTT GCT CCA
    Val Val Asn Ser Val Leu Ala Ser Ala Leu Ala Leu Thr Val Ala Pro
                                  10

49 ATG GCT TTC GCA GCA GAA GAA GCA GCA ACT ACT ACA GCT CCA AAA ATG
    Met Ala Phe Ala Ala Glu Glu Ala Ala Thr Thr Thr Ala Pro Lys Met
                    20                                  30

97 GAC GCT GAT ATG GAA AAA ACC GTA CAT CAT CAT CAT CAT CAC AAC TCT
    Asp Ala Asp Met Glu Lys Thr Val His His His His His His Asn Ser
                                  40

145 GAC TCC GAA TGC CCG CTG TCT CAC GAC GGT TAT TGC CTG CAT GAT GGT
    Asp Ser Glu Cys Pro Leu Ser His Asp Gly Tyr Cys Leu His Asp Gly
         50                                  60

193 GTT TGT ATG TAT ATC GAA GCT CTG GAC AAA TAT GCT TGC AAC TGT GTT
    Val Cys Met Tyr Ile Glu Ala Leu Asp Lys Tyr Ala Cys Asn Cys Val
                    70                                         80

241 GTT GGT TAC ATC GGT GAG CGT TGC CAG TAT CGC GAC CTG AAA TGG TGG
    Val Gly Tyr Ile Gly Glu Arg Cys Gln Tyr Arg Asp Leu Lys Trp Trp
                                  90

289 GAA CTG CGT GAC TAT GAT ATC CCG ACC ACT GAA AAC CTG TAC TTC CAA
    Glu Leu Arg Asp Tyr Asp Ile Pro Thr Thr Glu Asn Leu Tyr Phe Gln
                   100                                       110

337 TCT GCT AAC TCA AAC CCG GCT ATG GCA CCC CGA GAA CGC AAA GCT GGC
    Ser Ala Asn Ser Asn Pro Ala Met Ala Pro Arg Glu Arg Lys Ala Gly
                                 120

385 TGC AAG AAT TTC TTC TGG AAG ACT TTC ACA TCC TGT TAG
    Cys Lys Asn Phe Phe Trp Lys Thr Phe Thr Ser Cys ***
        130                                       140
```

FIG. 4

MWPsp-MWPmp20-(His)₆-Linker-V8-Glucagon

```
  1 GTC GTT AAC AGT GTA TTG GCT AGT GCA CTC GCA CTT ACT GTT GCT CCA
    Val Val Asn Ser Val Leu Ala Ser Ala Leu Ala Leu Thr Val Ala Pro
                                10

49 ATG GCT TTC GCA GCA GAA GAA GCA GCA ACT ACT ACA GCT CCA AAA ATG
    Met Ala Phe Ala Ala Glu Glu Ala Ala Thr Thr Thr Ala Pro Lys Met
                    20                                  30

97 GAC GCT GAT ATG GAA AAA ACC GTA CAT CAT CAT CAT CAT CAC GGT TCT
    Asp Ala Asp Met Glu Lys Thr Val His His His His His His Gly Ser
                                40

145 CCA GTA CCT TCT GGA TTC CTG GAA CAC AGC CAA GGT ACT TTC ACA TCC
    Pro Val Pro Ser Gly Phe Leu Glu His Ser Gln Gly Thr Phe Thr Ser
        50                                          60

193 GAC TAC TCT AAA TAT CTG GAT TCC CGT CGC GCT CAA GAT TTC GTT CAA
    Asp Tyr Ser Lys Tyr Leu Asp Ser Arg Arg Ala Gln Asp Phe Val Gln
                        70                                      80

241 TGG CTG ATG AAC ACT TAA
    Trp Leu Met Asn Thr ***
``` pNU-PINS-1: X=MWPsp-MWPmp10-(His)$_6$-Linker-Met-Proinsulin
pNU-PINS-2: X=MWPsp-MWPmp10-Met-Proinsulin
pNU-STN: X=MWPsp-MWPmp20-(His)$_6$-EGF-TEV-Somatostatin28
pNU-GCN: X=MWPsp-MWPmp20-(His)$_6$-Linker-V8-Glucagon

FIG. 17

MWPsp-MWPmp20-TEV-G-GH

```
  1 GTC GTT AAC AGT GTA TTG GCT AGT GCA CTC GCA CTT ACT GTT GCT CCA   48
  1 Val Val Asn Ser Val Leu Ala Ser Ala Leu Ala Leu Thr Val Ala Pro   16

49 ATG GCT TTC GCA GCA GAA GAA GCA GCA ACT ACT ACA GCT CCA AAA ATG   96
 17 Met Ala Phe Ala Ala Glu Glu Ala Ala Thr Thr Thr Ala Pro Lys Met   32

97 GAC GCT GAT ATG GAA AAA ACC GTA GAC TAT GAT ATC CCG ACC ACT GAA  144
 33 Asp Ala Asp Met Glu Lys Thr Val Asp Tyr Asp Ile Pro Thr Thr Glu   48

145 AAC CTG TAC TTC CAA GGT TTC CCA ACC ATT CCC TTA TCC AGG CTT TTT  192
 49 Asn Leu Tyr Phe Gln Gly Phe Pro Thr Ile Pro Leu Ser Arg Leu Phe   64

193 GAC AAC GCT ATG CTC CGC GCC CAT CGT CTG CAC CAG CTG GCC TTT GAC  240
 65 Asp Asn Ala Met Leu Arg Ala His Arg Leu His Gln Leu Ala Phe Asp   80

241 ACC TAC CAG GAG TTT GAA GAA GCC TAT ATC CCA AAG GAA CAG AAG TAT  288
 81 Thr Tyr Gln Glu Phe Glu Glu Ala Tyr Ile Pro Lys Glu Gln Lys Tyr   96

289 TCA TTC CTG CAG AAC CCC CAG ACC TCC CTC TGT TTC TCA GAG TCT ATT  336
 97 Ser Phe Leu Gln Asn Pro Gln Thr Ser Leu Cys Phe Ser Glu Ser Ile  112

337 CCG ACA CCC TCC AAC AGG GAG GAA ACA CAA CAG AAA TCC AAC CTA GAG  384
113 Pro Thr Pro Ser Asn Arg Glu Glu Thr Gln Gln Lys Ser Asn Leu Glu  128

385 CTG CTC CGC ATC TCC CTG CTG CTC ATC CAG TCG TGG CTG GAG CCC GTG  432
129 Leu Leu Arg Ile Ser Leu Leu Leu Ile Gln Ser Trp Leu Glu Pro Val  144

433 CAG TTC CTC AGG AGT GTC TTC GCC AAC AGC CTG GTG TAC GGC GCC TCT  480
145 Gln Phe Leu Arg Ser Val Phe Ala Asn Ser Leu Val Tyr Gly Ala Ser  160

481 GAC AGC AAC GTC TAT GAC CTC CTA AAG GAC CTA GAG GAA GGC ATC CAA  528
161 Asp Ser Asn Val Tyr Asp Leu Leu Lys Asp Leu Glu Glu Gly Ile Gln  176

529 ACG CTG ATG GGG AGG CTG GAA GAT GGC AGC CCC CGG ACT GGG CAG ATC  576
177 Thr Leu Met Gly Arg Leu Glu Asp Gly Ser Pro Arg Thr Gly Gln Ile  192

577 TTC AAG CAG ACC TAC AGC AAG TTC GAC ACA AAC TCA CAC AAC GAT GAC  624
193 Phe Lys Gln Thr Tyr Ser Lys Phe Asp Thr Asn Ser His Asn Asp Asp  208

625 GCA CTA CTC AAG AAC TAC GGG CTG CTC TAC TGC TTC AGG AAG GAC ATG  672
209 Ala Leu Leu Lys Asn Tyr Gly Leu Leu Tyr Cys Phe Arg Lys Asp Met  224

673 GAC AAG GTC GAG ACA TTC CTG CGC ATC GTG CAG TGC CGC TCT GTG GAG  720
225 Asp Lys Val Glu Thr Phe Leu Arg Ile Val Gln Cys Arg Ser Val Glu  240

721 GGC AGC TGT GGC TTC TAG                                           738
241 Gly Ser Cys Gly Phe ***                                           246
``` pNU-G-GH: X=MWPsp-MWPmp20-TEV-G-GH

SEQUENCE LISTING

<160> NUMBER OF SEQ ID NOS: 66

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Designated is a linker useful for expression and secretion of a fusion protein

<400> SEQUENCE: 1

Gly Ser Pro Val Pro Ser Gly

```
                 1               5
```

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Designated
      is a sequence required for cleaving out a polypeptide of interest
      with TEV protease

<400> SEQUENCE: 2

```
Asp Tyr Asp Ile Pro Thr Thr Glu Asn Leu Tyr Phe Gln
 1               5                  10
```

<210> SEQ ID NO 3
<211> LENGTH: 10
<212> TYPE: PRT
<213> ORGANISM: Bacillus brevis
<300> PUBLICATION INFORMATION:
<303> JOURNAL: J. Bacteriol.
<304> VOLUME: 169
<306> PAGES: 1239-1245
<307> DATE: 1987

<400> SEQUENCE: 3

```
Ala Glu Glu Ala Ala Thr Thr Thr Ala Pro
 1               5                  10
```

<210> SEQ ID NO 4
<211> LENGTH: 10
<212> TYPE: PRT
<213> ORGANISM: Bacillus brevis
<300> PUBLICATION INFORMATION:
<303> JOURNAL: J. Bacteriol.
<304> VOLUME: 170
<306> PAGES: 176-186
<307> DATE: 1988

<400> SEQUENCE: 4

```
Ala Pro Lys Asp Gly Ile Tyr Ile Gly Gly
 1               5                  10
```

<210> SEQ ID NO 5
<211> LENGTH: 10
<212> TYPE: PRT
<213> ORGANISM: Bacillus brevis
<300> PUBLICATION INFORMATION:
<303> JOURNAL: J. Bacteriol.
<304> VOLUME: 172
<306> PAGES: 1312-1320
<307> DATE: 1990

<400> SEQUENCE: 5

```
Ala Glu Asp Thr Thr Thr Ala Pro Lys Met
 1               5                  10
```

<210> SEQ ID NO 6
<211> LENGTH: 20
<212> TYPE: DNA
<213> ORGANISM: Bacillus brevis
<300> PUBLICATION INFORMATION:
<303> JOURNAL: J. Bacteriol.
<304> VOLUME: 169
<306> PAGES: 1239-1245
<307> DATE: 1987

<400> SEQUENCE: 6
gtcgttaaca gtgtattgct                                                    20

<210> SEQ ID NO 7
<211> LENGTH: 30
<212> TYPE: DNA
<213> ORGANISM: Bacillus brevis
<300> PUBLICATION INFORMATION:
<303> JOURNAL: J. Bacteriol.
<304> VOLUME: 170
<306> PAGES: 935-945
<307> DATE: 1988

<400> SEQUENCE: 7
tggagctgta gtagttgctg cttcttctgc                                          30

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Designated
      is a forward oligonucleotide encoding (His)6

<400> SEQUENCE: 8
catcatcatc atcatcac                                                       18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse oligonucleotide encoding (His)6

<400> SEQUENCE: 9
gtgatgatga tgatgatg                                                       18

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Designated
      is a reverse oligonucleotide encoding the linker Gly Ser Pro Val
      Pro Ser Gly

<400> SEQUENCE: 10
tccagaaggt actggagaac c                                                   21

<210> SEQ ID NO 11
<211> LENGTH: 19
<212> TYPE: DNA
<213> ORGANISM: Homo sapiens
<300> PUBLICATION INFORMATION:
<303> JOURNAL: Nature
<304> VOLUME: 282
<306> PAGES: 525-527
<307> DATE: 1979

<400> SEQUENCE: 11
atggccctgt ggatgcgcc                                                      19

<210> SEQ ID NO 12
<211> LENGTH: 19
<212> TYPE: DNA
<213> ORGANISM: Homo sapiens
<300> PUBLICATION INFORMATION:
<303> JOURNAL: Nature
<304> VOLUME: 282

```
<306> PAGES: 525-527
<307> DATE: 1979

<400> SEQUENCE: 12
ctagttgcag tagttctcc                                              19

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Designated
      is a forward primer for PCR amplification of human proinsulin DNA

<400> SEQUENCE: 13
tttgtgaacc aacacctg                                               18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp6 DNA

<400> SEQUENCE: 14
agttgctgct tcttctgc                                               18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp8 DNA

<400> SEQUENCE: 15
tgtagtagtt gctgcttc                                               18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp9 DNA

<400> SEQUENCE: 16
agctgtagta gttgctgc                                               18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp11 DNA

<400> SEQUENCE: 17
ttttggagct gtagtagt                                               18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Designated
``` is a reverse primer for PCR amplification of MWPsp-MWPmp12 DNA

<400> SEQUENCE: 18
catttttgga gctgtagt                                                        18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp15 DNA

<400> SEQUENCE: 19
atcagcgtcc attttttgg                                                       18

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp40 DNA

<400> SEQUENCE: 20
gtctacaccg tattcgccgt                                                      20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp50 DNA

<400> SEQUENCE: 21
agtagcgaac tctgcacgag                                                      20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp100 DNA

<400> SEQUENCE: 22
agatttgtcc gggaaacctt                                                      20

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse primer for PCR amplification of
      (His)6-Linker-Met-Proinsulin DNA

<400> SEQUENCE: 23
ctagttgcag tagttctc                                                        18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Designated is a reverse primer for PCR amplification of MWPsp-MWPmp1 DNA

<400> SEQUENCE: 24
tgctgcgaaa gccattgg                                                18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp2 DNA

<400> SEQUENCE: 25
tgctgcgaaa gccattgg                                                18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp3 DNA

<400> SEQUENCE: 26
ttcttctgct gcgaaagc                                                18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp4 DNA

<400> SEQUENCE: 27
tgcttcttct gctgcgaa                                                18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp5 DNA

<400> SEQUENCE: 28
tgctgcttct tctgctgc                                                18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp7 DNA

<400> SEQUENCE: 29
agtagttgct gcttcttc                                                18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp13 DNA

```
<400> SEQUENCE: 30
gtccattttt ggagctgt                                                18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp14 DNA

<400> SEQUENCE: 31
agcgtccatt tttggagc                                                18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp 17 DNA

<400> SEQUENCE: 32
ttccatatca gcgtccat                                                18

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp20 DNA

<400> SEQUENCE: 33
tacggttttt tccatatcag c                                            21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp DNA

<400> SEQUENCE: 34
tgcgaaagcc attggagcaa c                                            21

<210> SEQ ID NO 35
<211> LENGTH: 18
<212> TYPE: DNA
<213> ORGANISM: Homo sapiens

<400> SEQUENCE: 35
tctgctaact caaacccg                                                18

<210> SEQ ID NO 36
<211> LENGTH: 21
<212> TYPE: DNA
<213> ORGANISM: Homo sapiens

<400> SEQUENCE: 36
ctaacaggat gtgaaagtct t                                            21

<210> SEQ ID NO 37
<211> LENGTH: 18
```

```
<212> TYPE: DNA
<213> ORGANISM: Homo sapiens

<400> SEQUENCE: 37
aactctgact ccgaatgc                                              18

<210> SEQ ID NO 38
<211> LENGTH: 18
<212> TYPE: DNA
<213> ORGANISM: Homo sapiens

<400> SEQUENCE: 38
acgcagttcc caccattt                                              18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Designated
      is a reverse primer for PCR amplification of
      MWPsp-MWPmp10-(His)6-TEV DNA

<400> SEQUENCE: 39
ttggaagtac aggttttc                                              18

<210> SEQ ID NO 40
<211> LENGTH: 18
<212> TYPE: DNA
<213> ORGANISM: Homo sapiens

<400> SEQUENCE: 40
cacagccaag gtactttc                                              18

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Designated
      is a reverse primer for PCR amplification of human glucagon DNA

<400> SEQUENCE: 41
ttaagtgttc atcagccatt g                                          21

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Designated
      is a forward primer for PCR amplification of V8-Glucagon DNA

<400> SEQUENCE: 42
ttcctggaac acagccaa                                              18

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Designated
      is a reverse primer for PCR amplification of MWPsp-MWPmp30 DNA

<400> SEQUENCE: 43
tgctaccagg ccaagagctt                                            20
```

```
<210> SEQ ID NO 44
<211> LENGTH: 20
<212> TYPE: DNA
<213> ORGANISM: Homo sapiens
<300> PUBLICATION INFORMATION:
<303> JOURNAL: Nucleic Acids Res.
<304> VOLUME: 7
<306> PAGES: 305-320
<307> DATE: 1979

<400> SEQUENCE: 44
atggctacag gctcccggac                                                    20

<210> SEQ ID NO 45
<211> LENGTH: 20
<212> TYPE: DNA
<213> ORGANISM: Homo sapiens
<300> PUBLICATION INFORMATION:
<303> JOURNAL: Science
<304> VOLUME: 205
<306> PAGES: 602-607
<307> DATE: 1979

<400> SEQUENCE: 45
ctagaagcca cagctgccct                                                    20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Designated
      is a forward primer for PCR amplification of human growth hormone
      DNA

<400> SEQUENCE: 46
ttcccaacca ttcccttatc                                                    20

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Designated
      is a forward primer for PCR amplification of DNA for mutant human
      growth hormone with Gly at the N-terminus (G-GH)

<400> SEQUENCE: 47
ggtttcccaa ccattccctt atc                                                23

<210> SEQ ID NO 48
<211> LENGTH: 390
<212> TYPE: DNA
<213> ORGANISM: Artificial Sequence
<220> FEATURE:
<223> OTHER INFORMATION: Description of Artificial Sequence: Designated
      is a nucleotide sequence encoding
      MWPsp-MWPmp10-(His)6-Linker-Met-Proinsulin

<400> SEQUENCE: 48
gtcgttaaca gtgtattggc tagtgcactc gcacttactg ttgctccaat ggctttcgca        60
gcagaagaag cagcaactac tacagctcca catcatcatc atcatcacgg ttctccagta       120
ccttctggaa tgtttgtgaa ccaacacctg tgcggctcac acctggtgga agctctctac       180
ctagtgtgcg gggaaagagg cttcttctac acacccaaga cccgccggga ggcagaggac       240
```

```
ctgcaggtgg ggcaggtgga gctgggcggg ggccctggtg caggcagcct gcagcccttg      300
gccctggagg ggtccctgca gaagcgtggc attgtggaac aatgctgtac cagcatctgc      360
tccctctacc agctggagaa ctactgcaac                                        390
```

<210> SEQ ID NO 49
<211> LENGTH: 351
<212> TYPE: DNA
<213> ORGANISM: Artificial Sequence
<220> FEATURE:
<223> OTHER INFORMATION: Description of Artificial Sequence: Designated
      is a nucleotide sequence encoding MWPsp-MWPmp10-Met-Proinsulin

<400> SEQUENCE: 49

```
gtcgttaaca gtgtattggc tagtgcactc gcacttactg ttgctccaat ggctttcgca       60
gcagaagaag cagcaactac tacagctcca atgtttgtga accaacacct gtgcggctca      120
cacctggtgg aagctctcta cctagtgtgc ggggaaagag gcttcttcta cacacccaag      180
acccgccggg aggcagagga cctgcaggtg gggcaggtgg agctgggcgg gggccctggt      240
gcaggcagcc tgcagccctt ggccctggag ggtccctgc agaagcgtgg cattgtggaa       300
caatgctgta ccagcatctg ctccctctac agctggagaa actactgcaa c              351
```

<210> SEQ ID NO 50
<211> LENGTH: 420
<212> TYPE: DNA
<213> ORGANISM: Artificial Sequence
<220> FEATURE:
<223> OTHER INFORMATION: Description of Artificial Sequence: Designated
      is a nucleotide sequence encoding
      MWPsp-MWPmp20-(His)6-EGF-TEV-Somatostatin 28

<400> SEQUENCE: 50

```
gtcgttaaca gtgtattggc tagtgcactc gcacttactg ttgctccaat ggctttcgca       60
gcagaagaag cagcaactac tacagctcca aaaatggacg ctgatatgga aaaaccgta      120 catcatcatc atcatcacaa ctctgactcc gaatgcccgc tgtctcacga cggttattgc      180
ctgcatgatg gtgtttgtat gtatatcgaa gctctggaca aatatgcttg caactgtgtt      240
gttggttaca tcggtgagcg ttgccagtat cgcgacctga atggtgggga actgcgtgac      300
tatgatatcc cgaccactga aaacctgtac ttccaatctg ctaactcaaa cccggctatg      360
gcaccccgag aacgcaaagc tggctgcaag aatttcttct ggaagacttt cacatcctgt      420
```

<210> SEQ ID NO 51
<211> LENGTH: 255
<212> TYPE: DNA
<213> ORGANISM: Artificial Sequence
<220> FEATURE:
<223> OTHER INFORMATION: Description of Artificial Sequence: Designated
      is a nucleotide sequence encoding
      MWPsp-MWPmp20-(His)6-Linker-V8-Glucagon

<400> SEQUENCE: 51

```
gtcgttaaca gtgtattggc tagtgcactc gcacttactg ttgctccaat ggctttcgca       60
gcagaagaag cagcaactac tacagctcca aaaatggacg ctgatatgga aaaaccgta      120 catcatcatc atcatcacgg ttctccagta ccttctggat cctggaaca cagccaaggt      180 actttcacat ccgactactc taaatatctg gattccgtc gcgctcaaga tttcgttcaa      240
tggctgatga acact                                                       255
```

<210> SEQ ID NO 52

```
<211> LENGTH: 735
<212> TYPE: DNA
<213> ORGANISM: Artificial Sequence
<220> FEATURE:
<223> OTHER INFORMATION: Description of Artificial Sequence: Designated
      is a nucleotide sequence encoding MWPsp-MWPmp20-TEV-G-GH

<400> SEQUENCE: 52
gtcgttaaca gtgtattggc tagtgcactc gcacttactg ttgctccaat ggctttcgca      60
gcagaagaag cagcaactac tacagctcca aaaatggacg ctgatatgga aaaaaccgta    120
gactatgata tcccgaccac tgaaaacctg tacttccaag gtttcccaac cattccctta   180
tccaggcttt ttgacaacgc tatgctccgc gcccatcgtc tgcaccagct ggcctttgac   240
acctaccagg agtttgaaga agcctatatc caaaggaac agaagtattc attcctgcag    300 aaccccccaga cctccctctg tttctcagag tctattccga caccctccaa cagggaggaa    360
acacaacaga atccaacct agagctgctc cgcatctccc tgctgctcat ccagtcgtgg     420
ctggagcccg tgcagttcct caggagtgtc ttcgccaaca gcctggtgta cggcgcctct    480
gacagcaacg tctatgacct cctaaaggac ctagaggaag catccaaac gctgatgggg     540 aggctggaag atggcagccc ccggactggg cagatcttca gcagaccta cagcaagttc     600 gacacaaact cacacaacga tgacgcacta ctcaagaact acgggctgct ctactgcttc    660
aggaaggaca tggacaaggt cgagacattc ctgcgcatcg tgcagtgccg ctctgtggag    720
ggcagctgtg gcttc                                                     735

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Designated
      is a forward oligonucleotide encoding the linker
      Gly Ser Pro Val Pro Ser Gly

<400> SEQUENCE: 53
ggttctccag taccttctgg a                                               21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Designated
      is a forward oligonucleotide for PCR amplification of
      Met-Proinsulin DNA

<400> SEQUENCE: 54
atgtttgtga accaacacct g                                               21

<210> SEQ ID NO 55
<211> LENGTH: 87
<212> TYPE: DNA
<213> ORGANISM: Homo sapiens

<400> SEQUENCE: 55
tctgctaact caaacccggc tatggcaccc cgagaacgca agctggctg caagaatttc      60 ttctggaaga ctttcacatc ctgttag                                         87

<210> SEQ ID NO 56
<211> LENGTH: 169
<212> TYPE: DNA
```

<213> ORGANISM: Homo sapiens

<400> SEQUENCE: 56

```
aactctgact ccgaatgccc gctgtctcac gacggttatt gcctgcatga tggtgtttgt      60
atgtatatcg aagctctgga caaatatgct tgcaactgtg ttgttggtta catcggtgag     120
cgttgccagt atcgcgacct gaaatggtgg gaactgcgtt ctgctaact                 169
```

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence: Designated
is a forward oligonucleotide encoding an amino acid sequence
recognized by TEV protease

<400> SEQUENCE: 57

```
gactatgata tcccgaccac tgaaaacctg tacttccaa                             39
```

<210> SEQ ID NO 58
<211> LENGTH: 39
<212> TYPE: DNA
<213> ORGANISM: Artificial Sequence
<220> FEATURE:
<223> OTHER INFORMATION: Description of Artificial Sequence: Designated
is a reverse oligonucleotide encoding an amino acid sequence
recognized by TEV protease

<400> SEQUENCE: 58

```
ttggaagtac aggttttcag tggtcgggat atcatagtc                             39
```

<210> SEQ ID NO 59
<211> LENGTH: 87
<212> TYPE: DNA
<213> ORGANISM: Homo sapiens

<400> SEQUENCE: 59

```
cacagccaag gtactttcac atccgactac tctaaatatc tggattcccg tcgcgctcaa      60
gatttcgttc aatggctgat gaacact                                          87
```

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Designated
is a forward primer for PCR amplification of TEV-G-GH DNA

<400> SEQUENCE: 60

```
gactatgata tcccgaccac t                                                21
```

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Designated
is a tag for separation/purification of a fusion protein

<400> SEQUENCE: 61

His His His His His His
 1               5

<210> SEQ ID NO 62

```
<211> LENGTH: 130
<212> TYPE: PRT
<213> ORGANISM: Artificial Sequence
<220> FEATURE:
<223> OTHER INFORMATION: Description of Artificial Sequence: Designated
      is an amino acid sequence of
      MWPsp-MWPmp10-(His)6-Linker-Met-Proinsulin

<400> SEQUENCE: 62
```

Val Val Asn Ser Val Leu Ala Ser Ala Leu Ala Leu Thr Val Ala Pro
 1               5                  10                  15

Met Ala Phe Ala Ala Glu Glu Ala Ala Thr Thr Thr Ala Pro His His
             20                  25                  30

His His His His Gly Ser Pro Val Pro Ser Gly Met Phe Val Asn Gln
         35                  40                  45

His Leu Cys Gly Ser His Leu Val Glu Ala Leu Tyr Leu Val Cys Gly
     50                  55                  60

Glu Arg Gly Phe Phe Tyr Thr Pro Lys Thr Arg Arg Glu Ala Glu Asp
 65                  70                  75                  80

Leu Gln Val Gly Gln Val Glu Leu Gly Gly Gly Pro Gly Ala Gly Ser
                 85                  90                  95

Leu Gln Pro Leu Ala Leu Glu Gly Ser Leu Gln Lys Arg Gly Ile Val
                100                 105                 110

Glu Gln Cys Cys Thr Ser Ile Cys Ser Leu Tyr Gln Leu Glu Asn Tyr
            115                 120                 125

Cys Asn
    130

```
<210> SEQ ID NO 63
<211> LENGTH: 117
<212> TYPE: PRT
<213> ORGANISM: Artificial Sequence
<220> FEATURE:
<223> OTHER INFORMATION: Description of Artificial Sequence: Designated
      is an amino acid sequence of MWPsp-MWPmp10-Met-Proinsulin

<400> SEQUENCE: 63
```

Val Val Asn Ser Val Leu Ala Ser Ala Leu Ala Leu Thr Val Ala Pro
 1               5                  10                  15

Met Ala Phe Ala Ala Glu Glu Ala Ala Thr Thr Thr Ala Pro Met Phe
             20                  25                  30

Val Asn Gln His Leu Cys Gly Ser His Leu Val Glu Ala Leu Tyr Leu
             35                  40                  45

Val Cys Gly Glu Arg Gly Phe Phe Tyr Thr Pro Lys Thr Arg Arg Glu
     50                  55                  60

Ala Glu Asp Leu Gln Val Gly Gln Val Glu Leu Gly Gly Gly Pro Gly
 65                  70                  75                  80

Ala Gly Ser Leu Gln Pro Leu Ala Leu Glu Gly Ser Leu Gln Lys Arg
                 85                  90                  95

Gly Ile Val Glu Gln Cys Cys Thr Ser Ile Cys Ser Leu Tyr Gln Leu
                100                 105                 110

Glu Asn Tyr Cys Asn
            115

```
<210> SEQ ID NO 64
<211> LENGTH: 140
<212> TYPE: PRT
<213> ORGANISM: Artificial Sequence
<220> FEATURE:
<223> OTHER INFORMATION: Description of Artificial Sequence: Designated
```

US 6,506,595 B2

61                                                                                   62

-continued

```
      is an amino acid sequence of
      MWPsp-MWPmp20-(His)6-EGF-TEV-Somatostatin 28

<400> SEQUENCE: 64

Val Val Asn Ser Val Leu Ala Ser Ala Leu Ala Leu Thr Val Ala Pro
  1               5                  10                  15

Met Ala Phe Ala Ala Glu Glu Ala Ala Thr Thr Thr Ala Pro Lys Met
             20                  25                  30

Asp Ala Asp Met Glu Lys Thr Val His His His His His His Asn Ser
         35                  40                  45

Asp Ser Glu Cys Pro Leu Ser His Asp Gly Tyr Cys Leu His Asp Gly
     50                  55                  60

Val Cys Met Tyr Ile Glu Ala Leu Asp Lys Tyr Ala Cys Asn Cys Val
 65                  70                  75                  80

Val Gly Tyr Ile Gly Glu Arg Cys Gln Tyr Arg Asp Leu Lys Trp Trp
             85                  90                  95

Glu Leu Arg Asp Tyr Asp Ile Pro Thr Thr Glu Asn Leu Tyr Phe Gln
            100                 105                 110

Ser Ala Asn Ser Asn Pro Ala Met Ala Pro Arg Glu Arg Lys Ala Gly
            115                 120                 125

Cys Lys Asn Phe Phe Trp Lys Thr Phe Thr Ser Cys
            130                 135                 140

<210> SEQ ID NO 65
<211> LENGTH: 85
<212> TYPE: PRT
<213> ORGANISM: Artificial Sequence
<220> FEATURE:
<223> OTHER INFORMATION: Description of Artificial Sequence: Designated
      is an amino acid sequence of
      MWPsp-MWPmp20-(His)6-Linker-V8-Glucagon

<400> SEQUENCE: 65

Val Val Asn Ser Val Leu Ala Ser Ala Leu Ala Leu Thr Val Ala Pro
  1               5                  10                  15

Met Ala Phe Ala Ala Glu Glu Ala Ala Thr Thr Thr Ala Pro Lys Met
             20                  25                  30

Asp Ala Asp Met Glu Lys Thr Val His His His His His Gly Ser
         35                  40                  45

Pro Val Pro Ser Gly Phe Leu Glu His Ser Gln Gly Thr Phe Thr Ser
     50                  55                  60

Asp Tyr Ser Lys Tyr Leu Asp Ser Arg Arg Ala Gln Asp Phe Val Gln
 65                  70                  75                  80

Trp Leu Met Asn Thr
             85

<210> SEQ ID NO 66
<211> LENGTH: 245
<212> TYPE: PRT
<213> ORGANISM: Artificial Sequence
<220> FEATURE:
<223> OTHER INFORMATION: Description of Artificial Sequence: Designated
      is an amino acid sequence of MWPsp-MWPmp20-TEV-G-GH

<400> SEQUENCE: 66

Val Val Asn Ser Val Leu Ala Ser Ala Leu Ala Leu Thr Val Ala Pro
  1               5                  10                  15

Met Ala Phe Ala Ala Glu Glu Ala Ala Thr Thr Thr Ala Pro Lys Met
             20                  25                  30
```

-continued

```
Asp Ala Asp Met Glu Lys Thr Val Asp Tyr Asp Ile Pro Thr Thr Glu
        35                  40                  45

Asn Leu Tyr Phe Gln Gly Phe Pro Thr Ile Pro Leu Ser Arg Leu Phe
        50                  55                  60

Asp Asn Ala Met Leu Arg Ala His Arg Leu His Gln Leu Ala Phe Asp
65              70                  75                      80

Thr Tyr Gln Glu Phe Glu Glu Ala Tyr Ile Pro Lys Glu Gln Lys Tyr
                85                  90                  95

Ser Phe Leu Gln Asn Pro Gln Thr Ser Leu Cys Phe Ser Glu Ser Ile
            100                 105             110

Pro Thr Pro Ser Asn Arg Glu Glu Thr Gln Gln Lys Ser Asn Leu Glu
        115                 120                 125

Leu Leu Arg Ile Ser Leu Leu Leu Ile Gln Ser Trp Leu Glu Pro Val
    130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

Thr Leu Met Gly Arg Leu Glu Asp Gly Ser Pro Arg Thr Gly Gln Ile
            180                 185                 190

Phe Lys Gln Thr Tyr Ser Lys Phe Asp Thr Asn Ser His Asn Asp Asp
        195                 200                 205

Ala Leu Leu Lys Asn Tyr Gly Leu Leu Tyr Cys Phe Arg Lys Asp Met
    210                 215                 220

Asp Lys Val Glu Thr Phe Leu Arg Ile Val Gln Cys Arg Ser Val Glu
225             230                 235                 240

Gly Ser Cys Gly Phe
                245
```

DNAS ENCODING NEW FUSION PROTEINS AND PROCESSES FOR PREPARING USEFUL POLYPEPTIDES THROUGH EXPRESSION OF THE DNAS

TECHNICAL FIELD

This invention relates to DNAs encoding new fusion proteins, and to use of the DNAs in production of biologically active polypeptides utilizable in the fields of pharmaceuticals and researches as well as in other industries.

BACKGROUND OF INVENTION

Polypeptide substances, e.g., hormones and physiologically active substances as pharmaceuticals, and enzymes for diagnosis, industrial uses and researches, have often been obtained from organisms by means of extraction methods. However, it is difficult to obtain a pure substance in a large amount at a low cost by extraction. Recently, owing to progress of gene recombination techniques, highly pure recombinant proteins have been prepared more economically in a larger amount by use of various cells from organisms such as microorganisms, animals and plants.

However, economical mass production of useful proteins (or polypeptides) has not yet been achieved completely, and development of new techniques has therefore been carried out continuously. In addition, mass production systems developed until now are not capable of producing all kinds of proteins by gene recombination techniques, thus they have in practice been developed individually depending upon the kind of protein.

In an expression system for recombinant proteins using Bacillus brevis, when an exogenous protein is attached to follow a signal peptide for cell wall protein (referred to as "CWP") of the microorganism and the resultant fusion protein is expressed, the exogenous protein with a natural type structure is cut away from the CWP signal peptide to be secreted in a medium (Japanese Patent No. 2082727; JP-A-62-201583; Yamagata, H. et al., J. Bacteriol. 169:1239–1245 (1987); Udaka, J., Journal of Japan Society for Bioscience, Biotechnology, and Agrochemistry, 61:669–676 (1987); Takano, M. et al., Appl. Microbiol. Biotechnol. 30:75–80 (1989); and Yamagata, H. et al., Proc. Natl. Acad. Sci. USA 86:3589–3593 (1989)). When human epidermal growth factor (referred to as "EGF") is expressed in the above expression system, the expression amount is 10–100 fold higher than those of EGF expressed in other expression systems; the expressed protein is secreted in a medium while holding its original activity, therefore separation and purification of the protein is easy; and unlike some E. coli expression systems, this system does not require complicated procedures for conversion of an inactive protein into an active protein. For these reasons, the above-mentioned expression system has attracted attention as a mass production system of recombinant proteins.

However, not all proteins that were linked with the CWP signal peptide were expressed in an amount comparable to that found in EGF, and they were not always cleaved away from the signal peptide to be secreted in a medium.

A means to solve the above problem was suggested by Miyauchi et al. in Lecture Abstracts of the Annual Meeting of Japan Society for Bioscience, Biotechnology, and Agrochemistry, 67:372 (1993). That is, they prepared a gene encoding a fusion protein in which 17 amino acids (but unsuccessful with 9 or 12 amino acids) from the N-terminus of an MWP protein, one of CWPs, have been inserted between an MWP signal peptide and a flounder growth hormone protein, and expressed the gene in a Bacillus bacterium to obtain the fusion protein. The produced protein, however, was a nonnatural type protein with some amino acids added to the N-terminus. Miyauchi et al. suggested that the expression was influenced by the number of amino acids from the N-terminus of the MWP.

Miyauchi et al. neither teach nor suggest production of a polypeptide having the same amino acid composition as that of the corresponding natural type by utilizing introduction of a chemical or enzymatic cleavage site into its sequence. In fact, such a cleavage is difficult because the flounder growth hormone includes some sequences susceptible to chemical or enzymatic cleavage.

In this situation, it will be highly useful for an industrial purpose to develop a technique that facilitates expression and secretion of an exogenous polypeptide in a Bacillus expression system, i.e. a high expression system for recombinant proteins, where a polypeptide has the same sequence as the natural type.

The object of the present invention is to provide a Bacillus expression system comprising a DNA for a fusion protein containing a useful polypeptide sequence, the system having an ability to highly express and secrete the fusion protein which is selectively cleaved to give the polypeptide having a natural type structure.

SUMMARY OF INVENTION

The present invention provides a DNA comprising a nucleotide sequence encoding a fusion protein, wherein the fusion protein comprises: a sequence consisting of one or more amino acid residues from the N-terminus of a cell wall protein (CWP) from Bacillus bacterium; a sequence consisting of an amino acid residue or amino acid residues for chemical or enzymatic cleavage; and an exogenous polypeptide sequence, said sequences being linked linearly to one another in order, and wherein said nucleotide sequence is ligated to 3'-end of a nucleic acid sequence comprising a Bacillus promoter region.

The word "one or more amino acid residues from the N-terminus (of a cell wall protein)" as used herein means a sequence consisting of one or more amino acids from the N-terminal amino acid numbered as 1. For example, the sequence consisting of 3 amino acid residues refers to an amino acid sequence from number 1 to number 3 of the cell wall protein.

The fusion protein may further comprise a Bacillus CWP signal peptide sequence at the N-terminus.

The fusion protein may further comprise a sequence consisting of amino acid residues used as a tag for separation and purification and/or a sequence of amino acid residues used as a linker.

In an embodiment of the invention, the Bacillus bacterium is Bacillus brevis.

As the amino acid residue for chemical cleavage, exemplified is methionine. In this instance, the fusion protein should not contain additional methionine residues so that the highest specificity can be achieved in a chemical cleavage reaction, for example, with cyanogen bromide.

Amino acid residues for enzymatic cleavage can comprise a sequence capable of cleaving with a protease. Examples of the protease are TEV protease, V8 protease, etc.

In the first preferred embodiment of the invention, the fusion protein comprises: a sequence consisting of one or more amino acid residues from the N-terminus of an MWP protein which is one of CWPs; a sequence consisting of six histidine residues as a tag for separation and purification; an amino acid sequence, Gly Ser Pro Val Pro Ser Gly (SEQ ID NO:1), as a linker; a methionine residue required for chemically cleaving out a polypeptide of interest; and a polypeptide sequence containing no methionine in its amino acid sequence, said sequences being linked linearly to one another in order.

In this instance, the fusion protein may comprise an MWP signal peptide sequence at the N-terminus. And an example of the polypeptide is human proinsulin. The sequence consisting of one or more amino acid residues from the N-terminus of an MWP protein preferably comprises 6, 7, 8, 10, 11, 12, 13, 14, 15, 17, 20 or 50 amino acids.

In the second preferred embodiment of the invention, the fusion protein comprises: a sequence consisting of 10 or 20 amino acid residues from the N-terminus of an MWP protein which is one of CWPs; a sequence consisting of six histidine residues as a tag for separation and purification; a sequence of human epidermal growth factor as a linker; an amino acid sequence, Asp Tyr Asp Ile Pro Thr Thr Glu Asn Leu Tyr Phe Gln (SEQ ID NO:2), required for cleaving out a polypeptide of interest with TEV protease; and a polypeptide sequence that contains no TEV protease recognition sequence in its amino acid sequence and has glycine or serine at the N-terminus, said sequences being linked linearly to one another in order.

In this instance, the fusion protein may further comprise an MWP signal peptide sequence at the N-terminus. As the polypeptide, human somatostatin 28 is exemplified.

In the third preferred embodiment of the invention, the fusion protein comprises: a sequence consisting of 20 amino acid residues from the N-terminus of an MWP protein which is one of CWPs; a sequence consisting of six histidine residues as a tag for separation and purification; an amino acid sequence, Gly Ser Pro Val Pro Ser Gly, (SEQ ID NO: 1)as a linker; an amino acid sequence, Phe Leu Glu, required for cleaving out a polypeptide of interest with V8 protease; and a polypeptide sequence containing no glutamic acid in its amino acid sequence, said sequences being linked linearly to one another in order.

In this instance, similarly, the fusion protein may further comprise an MWP signal peptide sequence at the N-terminus. Human glucagon is useful as the polypeptide.

The present invention also provides a DNA comprising a nucleotide sequence encoding a fusion protein, wherein said fusion protein comprises: a CWP signal peptide sequence from a Bacillus bacterium; a sequence consisting of amino acid residues for enzymatic cleavage; and an exogenous polypeptide sequence, said sequences being linked linearly to one another in order, and wherein said nucleic acid sequence is ligated to 3'-end of a nucleotide sequence comprising a Bacillus promoter region.

In this invention, the signal peptide sequence may be directly followed by a sequence of one or more amino acid residues from the N-terminus of the CWP protein.

Preferably, the Bacillus bacterium is *Bacillus brevis*.

In an embodiment of the invention, the sequence consisting of amino acid residues for enzymatic cleavage comprises a sequence capable of cleaving with a protease.

In another embodiment of the invention, the fusion protein comprises: a signal peptide sequence for MWP which is one of CWPs; an amino acid sequence, Asp Tyr Asp Ile Pro Thr Thr Glu Asn Leu Tyr Phe Gln, (SEQ ID NO: 2) required for cleaving out a polypeptide of interest with TEV protease; and a polypeptide sequence that contains no TEV protease recognition sequence in its amino acid sequence, said sequences being linked linearly to one another in order.

In this instance, the signal peptide sequence may be directly followed by a sequence consisting of one or more amino acid residues from the N-terminus of the MWP protein. As the polypeptide, exemplified is a mutant human growth hormone with glycine or serine at the N-terminus.

The present invention further provides a vector comprising each of the DNAs as defined above.

The present invention still further provides a bacterium belonging to the genus Bacillus transformed with the above vector. The preferred bacterium is *Bacillus brevis*.

The present invention still yet further provides a process for preparing a recombinant polypeptide, comprising culturing the bacterium as defined above in a medium to accumulate, outside the bacterial cells, a fusion protein comprising an exogenous polypeptide; removing the fusion protein from the medium; cleaving out the polypeptide from the removed fusion protein; and recovering the polypeptide.

This specification includes all or part of the contents as disclosed in the specification and/or drawings of Japanese Patent Application No. 10-87339, which is a priority document of the present application.

BRIEF DESCRIPTION OF THE DRAWINGS

FIG. 1 shows an amino acid sequence of the fusion product MWPsp-MWPmp10-(His)$_6$-Linker-Met-Proinsulin, and a nucleotide sequence encoding the same.

FIG. 2 shows an amino acid sequence of the fusion product MWPsp-MWPmp10-Met-Proinsulin, and a nucleotide sequence encoding the same.

FIG. 3 shows an amino acid sequence of the fusion product MWPsp-MWPmp20-(His)$_6$-EGF-TEV-Somatostatin 28, and a nucleotide sequence encoding the same.

FIG. 4 shows an amino acid sequence of the fusion product MWPsp-MWPmp20-(His)$_6$-Linker-V8-Glucagon, and a nucleotide sequence encoding the same.

FIG. 17 shows an amino acid sequence of the fusion product MWPsp-MWPmp20-TEV-G-GH and a nucleotide sequence encoding the same.

DETAILED DESCRIPTION

Figure 5:
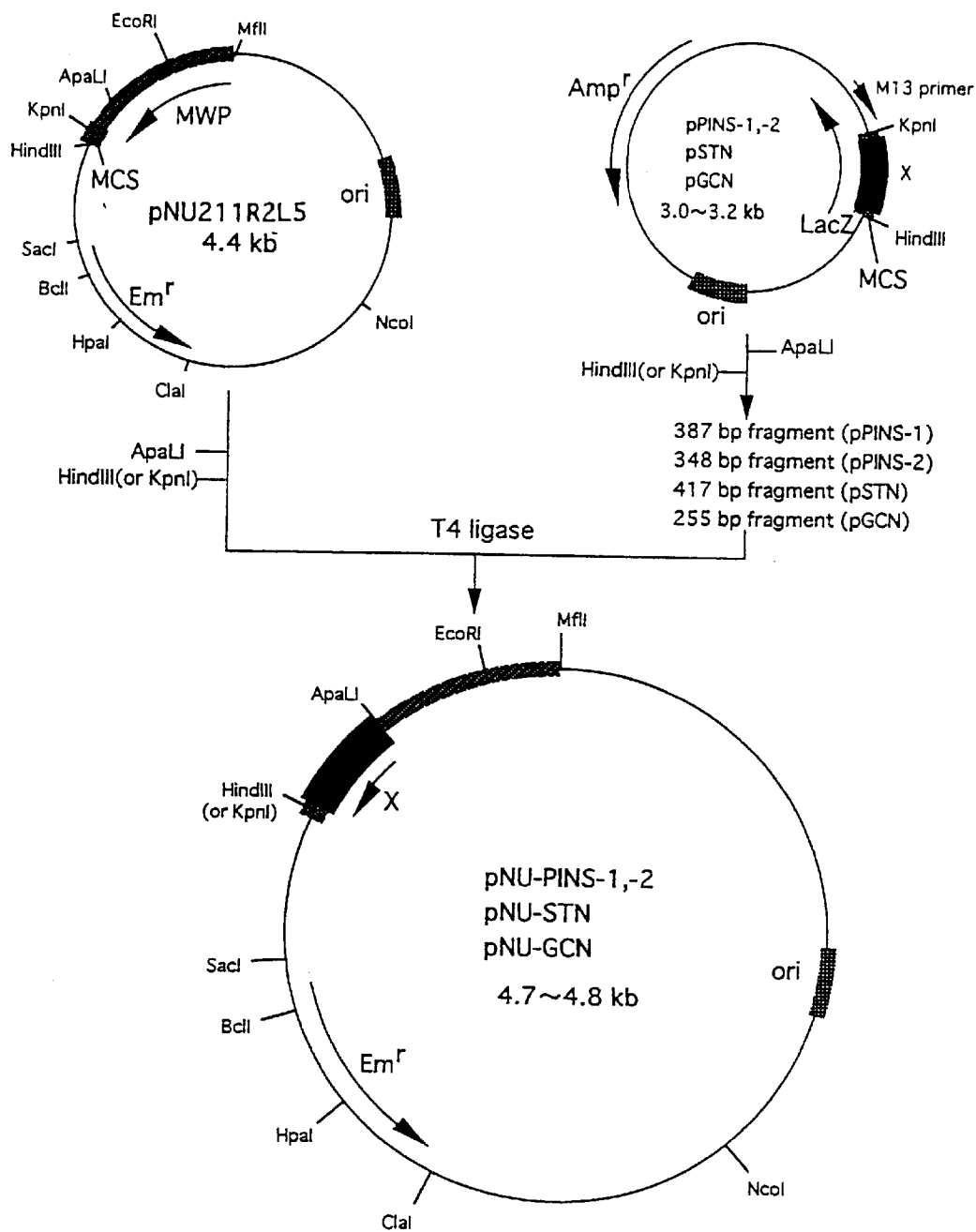
FIG. 5 is a schematic view for illustrating a manner of introducing each fusion DNA into *Bacillus brevis* expression vector (pNU211R2L5).

According to the present invention, a polypeptide with a desired natural type primary structure can be obtained by chemically or enzymatically treating a fusion protein produced through expression of the above-defined DNA in a Bacillus bacterium.

Examples of the one or more amino acid residues from the N-terminus of a CWP protein derived from a Bacillus bacterium, are amino acid residues from, but are not limited to, Bacillus brevis strain 47-5Q (Accession number FERM BP-1664; JP-A-60-58074, JP-A-62-201589) and Bacillus brevis strain HPD31 (Accession number FERM BP-1087; JP-A-04-278091). For example, the following sequences can be employed:

MWPmp10: Ala Glu Glu Ala Ala Thr Thr Thr Ala Pro (SEQ ID NO:3; J. Bacteriol. 169:1239–1245, 1989);

OWPmp10: Ala Pro Lys Asp Gly Ile Tyr Ile Gly Gly (SEQ ID NO:4; J. Bacteriol. 170:176–186, 1988);

HWPmp10: Ala Glu Asp Thr Thr Thr Ala Pro Lys Met (SEQ ID NO:5; J. Bacteriol. 172:1312–1320, 1990).

The number of amino acid residues from the N-terminus is generally 1 or more, preferably 6 or more, more preferably 6, 7, 8, 10, 11, 12, 13, 14, 15, 17, 20, or 50.

With respect to the amino acid residues for chemical or enzymatic cleavage, examples of the chemical cleavage include selective cleavages at the C-terminal side of methionine (J. Biol. Chem. 237:1856–1860, 1962) and at the C-terminal side of tryptophan (Methods in Enzymol. 91:318–324, 1983); and examples of the enzymatic cleavage are selective cleavages of a fusion site by Factor Xa, thrombin, enterokinase, V8 protease, TEV protease, or the like. Because an amino acid sequence for chemical or enzymatic cleavage is positioned at the N-terminal side of a polypeptide of interest, a subsequent chemical or enzymatic cleavage can result in production of the polypeptide with a desired primary structure.

In the present invention, the exogenous polypeptide may be from any origin of organisms as long as it is not affected by the above mentioned chemical or enzymatic cleavage procedures. More specifically, when the chemical cleavage, particularly cleavage with cyanogen bromide, is used, no methionine residue should be contained in a primary structure (or amino acid sequence) of an exogenous polypeptide of interest. Examples of such a polypeptide are, but are not limited to, human proinsulin, human platelet-derived growth factor A chain (PDGF-A), human secretin, and the like. When TEV protease is particularly used in the enzymatic cleavage, the exogenous polypeptide has to have a Gly or Ser residue at the N-terminal side in order to obtain a polypeptide identical to the natural type. Examples of such an exogenous polypeptide are human somatostatin 28, human platelet-derived growth factor A chain (PDGF-A), human nerve growth factor (NGF), and the like. However, the polypeptide is not limited to any of the above specific examples as long as addition of Gly or Ser to the N-terminus does not affect functions of an exogenous polypeptide. When V8 protease is used in the enzymatic cleavage, the exogenous polypeptide should never contain a Glu residue or Glu residues. Examples of such a polypeptide are human glucagon, human atrial natriuretic peptide, human calcitonin, and the like.

According to the present invention, the DNA can preferably comprise a nucleotide sequence encoding a Bacillus CWP signal peptide, particularly MWP signal peptide, at the N-terminus of the fusion protein.

The DNA of the invention can further contain a nucleotide sequence encoding amino acids used as a tag for separation and purification and/or a nucleotide sequence encoding amino acids named a linker.

As used herein, "tag for separation and purification" refers to a peptide for facilitating isolation of a fusion protein prepared through expression by gene recombination. It is preferred that the bonding between a tag and a substance capable of binding thereto is reversible. The tag includes, for example, glutathione S-transferase with affinity for glutathione, maltose-binding protein with affinity for amylose, a peptidic sequence of histidine residues where histidine has an affinity for a metal, an antigen or an antibody thereto, and the like. In one preferred embodiment of the invention, such a tag is His His His His His His (SEQ ID NO:61) (i.e., (His)$_6$).

In general, a linker is present between functional domains in a protein and has a function of linking the domains without affecting functions of the domains. In the present invention, the linker is positioned between a tag for separation and purification and an exogenous polypeptide and serves for expression/secretion of a fusion protein with the inserted tag. Examples of the linker used are combinations of different numbers of amino acid residues selected from Ala, Gly, Pro, Ser and Val. In a preferred embodiment of the invention, such a linker is Gly Ser Pro Val Pro Ser Gly (SEQ ID NO: 1). If, however, there is no tag to be inserted for separation and purification, the linker may or may not be incorporated into a fusion protein. In the case of a fusion protein comprising somatostatin 28 as an exogenous polypeptide, a particular linker, such as EGF, is essential for expression/secretion of the exogenous polypeptide.

In one embodiment of the present invention, the invention provides a DNA comprising a nucleotide sequence encoding a fusion protein, wherein the fusion protein comprises: a sequence consisting of 1 or more, preferably 6 to 50 (except 9), particularly 6, 7, 8, 10, 11, 12, 13, 14, 15, 17, 20 or 50 amino acid residues from the N-terminus of an MWP protein which is one of CWPs (hereinafter referred to as MWPmp6, MWPmp7, MWPmp8, MWPmp10and so on); a sequence consisting of six histidine residues as a tag for separation and purification (represented as (His)$_6$ (SEQ ID NO: 61) herein); an amino acid sequence, Gly Ser Pro Val Pro Ser Gly, (SEQ ID NO: 1) as a linker; a methionine residue required for chemically cleaving out a polypeptide of interest; and a polypeptide sequence containing no methionine in its amino acid sequence, said sequences being linked linearly to one another in order, and wherein the nucleotide sequence is ligated to 3'-end of a nucleic acid sequence comprising a Bacillus promoter region. An example of the polypeptide is human proinsulin. The tag or linker is an optional element. The fusion protein may further comprise an MWP signal peptide sequence at the N-terminus.

In another embodiment, the present invention provides a DNA comprising a nucleotide sequence encoding a fusion protein, wherein the fusion protein comprises: a sequence consisting of 1 or more, preferably 6 to 50 (except 9), particularly 10 or 20 amino acid residues from the N-terminus of an MWP protein which is one of CWPs; a sequence consisting of six histidine residues as a tag for separation and purification; a sequence of human epidermal growth factor as a linker; an amino acid sequence, Asp Tyr Asp Ile Pro Thr Thr Glu Asn Leu Tyr Phe Gln, (SEQ ID NO: 2) required for cleaving out a polypeptide of interest with TEV protease; and a polypeptide sequence that contains no TEV protease recognition sequence in its amino acid sequence and has glycine or serine at the N-terminus, said sequences being linked linearly to one another in order, and wherein the nucleotide sequence is linked to 3'-end of a nucleic acid sequence comprising a Bacillus promoter region. An example of the polypeptide is somatostatin 28. The fusion protein may further comprise an MWP signal peptide sequence at the N-terminus.

In still another embodiment, the present invention provides a DNA comprising a nucleotide sequence encoding a fusion protein, wherein the fusion protein comprises: a sequence consisting of 1 or more, preferably 6 to 50 (except 9), particularly 20 amino acid residues from the N-terminus of an MWP protein which is one of CWPs; a sequence consisting of six histidine residues as a tag for separation and purification; an amino acid sequence, Gly Ser Pro Val Pro Ser Gly, as a linker; an amino acid sequence, Phe Leu Glu, required for cleaving out a polypeptide of interest with V8 protease; and a polypeptide sequence containing no glutamic acid in its amino acid sequence, said sequences being linked linearly to one another in order, and wherein the nucleotide sequence is linked to 3'-end of a nucleic acid sequence comprising a Bacillus promoter region. An example of the polypeptide is human glucagon. The fusion protein may further comprise an MWP signal peptide sequence at the N-terminus.

According to another aspect of the invention, the present invention also relates to a DNA comprising a nucleotide sequence encoding a fusion protein, wherein said fusion protein comprises: a CWP signal peptide sequence from a Bacillus bacterium; a sequence consisting of amino acid residues for enzymatic cleavage; and an exogenous polypeptide sequence, said sequences being linked linearly to one another in order, and wherein said nucleotide sequence is ligated to 3'-end of a nucleic acid sequence comprising a Bacillus promoter region.

The signal peptide sequence may directly be followed by a sequence consisting of one or more amino acid residues from the N-terminus of the CWP protein. And the sequence for enzymatic cleavage can be susceptible to a protease such as Factor Xa, thrombin, enterokinase, V8 protease, or TEV protease.

In one embodiment of the invention, the fusion protein comprises: a signal peptide sequence for MWP which is one of CWPs; an amino acid sequence, Asp Tyr Asp Ile Pro Thr Thr Glu Asn Leu Tyr Phe Gln, (SEQ ID NO: 2) required for cleaving out a polypeptide of interest with TEV protease; and a polypeptide sequence that contains no TEV protease recognition sequence in its amino acid sequence, said sequences being linked linearly to one another in order.

In this instance, the signal peptide sequence may directly be followed by a sequence consisting of one or more amino acid residues from the N-terminus of the MWP protein. If the sequence from the N-terminus of the MWP protein is contained in the fusion protein, it preferably comprises 1, 2, 3, 4, 5, 6, 7, 8, 9, 10, 11, 12, 14, 20, or 30 amino acids. An example of the polypeptide is a mutant human growth hormone with glycine at the N-terminus.

In the present invention, the nucleotide sequence encoding the above mentioned fusion protein is ligated to 3'-end of a nucleic acid sequence comprising a Bacillus promoter region. Usable promoters are, but are not limited to, MWP promoter derived from *Bacillus brevis* strain 47-5Q (JP-B-01-58950; JP-B-07-108224), HWP promoter derived from *Bacillus brevis* strain HPD31 (JP-A-04-278091; JP-A-06-133782), and the like.

The DNA according to the invention can be prepared by combination of known techniques in the art. For instance, DNA sequences for elements can individually be prepared by chemical synthesis or cloning; and the obtained DNA sequences are ligated in order with a ligase to give a DNA of interest by combination of PCR (i.e., polymerase chain reaction) amplification. Details will be understood with reference to Examples as described below. With regard to respective general techniques which can be used in the present invention, see Maniatis, T. et al., Molecular Cloning Second Edition, A Laboratory Manual, Cold Spring Harbor Laboratory (1989); and Innis, N. A. et al., PCR Protocols, A guide to methods and applications, Academic Press (1990).

The DNA encoding an exogenous polypeptide is obtainable by utilizing conventional cloning techniques. For instance, the exogenous polypeptide is purified and determined for partial amino acid sequence; syntheses of probes or preparation of antibodies are carried out on the basis of the determined sequence; and a cDNA library containing a cDNA of interest is screened using the probes or antibodies, thereby obtaining a DNA encoding the polypeptide of interest. In case of a shorter DNA, it may be synthesized on a commercially available DNA synthesizer, utilizing, for example, phosphoramidite chemistry. If necessary, DNA may be subjected to a PCR amplification wherein a cycle of DNA denaturation, annealing with primers and elongation is repeated 20 times or more.

Figure 18:
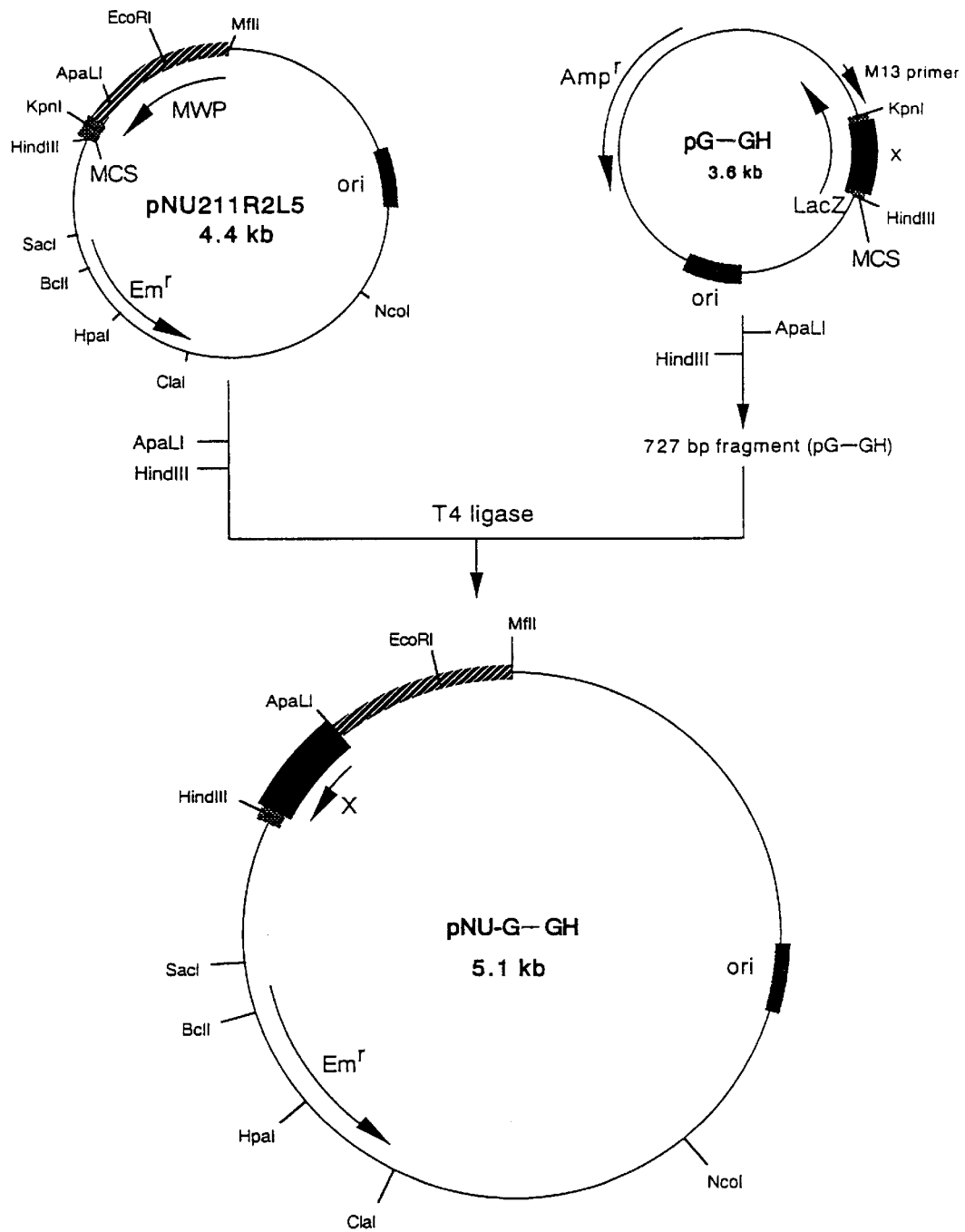
FIG. 18 is a schematic view for illustrating a manner of introducing the fusion product MWPsp-MWPmp20-TEV-G-GH into Bacillus brevis expression vector (pNU211R2L5).

The present invention further provides a vector comprising the above-defined DNA. Vectors, which can be used in the invention, have to at least contain an appropriate insertion site(s) or restriction site(s) capable of introducing the DNA, allow to express the DNA in Bacillus host cells, and be autonomously replicable in the host cells. The vector may contain an origin of replication, a terminator sequence, a ribosome binding site, or a selectable marker such as a drug resistance gene and a gene for complementing an auxotrophic character. Preferably, the vector of the invention is a plasmid. Examples of the vector include pNU200, pHY500 (Proc. Natl. Acad. Sci. USA 86:3589–3593, 1989), pHY4831 (J. Bacteriol. 169:1239–1245, 1987), pNU100 (Appl. Microbiol. Biotechnol. 30:75–80, 1989), pNU211 (J. Biochem. 112:488–491, 1992), pNU211R2L5 (JP-A-07-170984), pHY700 (JP-A-04-278091), pHT210 (JP-A-06-133782), and pHT11OR2L5 (Appl. Microbiol. Biotechnol. 42:358–363, 1994). In Examples as described below, the expression vectors, i.e. pNU-PINS-1, pNU-PINS-2, pNU-STN, pNU-GCN, and pNU-G-GH, can be prepared by the construction methods as shown in FIGS. 5 and 18.

The present invention still further provides a bacterium belonging to the genus Bacillus transformed with the above-defined vector. The Bacillus bacteria usable in the invention are, but are not limited to, *Bacillus brevis* strain 47-5Q (FERM BP-1664; JP-A-60-58074, JP-A-62-201589), *Bacillus brevis* strain 47K (JP-A-02-257876), *Bacillus brevis* strain 31 OK (JP-A-06-296485), *Bacillus brevis* strain HPD31 (FERM BP-1087; JP-A-04-278091), and the like. The expression vectors, i.e., pNU-PINS-1, pNU-PINS-2, pNU-STN and pNU-GCN, which were introduced into *Bacillus brevis* strain 47-5Q, have respectively been deposited under the Budapest treaty with the National Institute of Bioscience and Human-Technology, Agency of Industrial Science and Technology (1–3, Higashi 1-chome, Tsukuba-shi, Ibaraki-ken, Japan), under Accession Numbers: FERM BP-6311, FERM BP-6312, FERM BP-6313 and FERM BP-6314.

Vectors obtained as above are introduced into a competent Bacillus bacterial cell, which is then cultured in an appropriate medium under conditions enabling the vector to express, thereby producing a recombinant fusion polypeptide within or outside the cell, preferably outside the cell; and the produced polypeptide is recovered and purified by conventional methods. An example of the introduction is electroporation (Methods in Enzymol. 217:23–33, 1993). Purification of the obtained fusion protein can be carried out by appropriately combining gel filtration, ion-exchange chromatography, affinity chromatography, hydrophobic interaction chromatography, electrophoresis, and the like.

The fusion protein can subsequently be subjected to a chemical or enzymatic cleavage to give a polypeptide of interest with a natural type primary structure. For cleavage treatments, the chemical cleavage at the C-terminal side of methionine or tryptophan, as well as the enzymatic cleavage with Factor Xa, thrombin, enterokinase, V8 protease or TEV protease, can be used.

The present invention thus provides a process for preparing a recombinant polypeptide, comprising culturing a bacterium belonging to the genus Bacillus transformed as above in a medium to accumulate, outside the bacterial cells, a fusion protein comprising an exogenous polypeptide; removing the fusion protein from the medium; cleaving out the polypeptide from the removed fusion protein; and recovering the polypeptide.

Recombinant polypeptides produced by the process of the invention will be useful for pharmaceuticals, diagnoses, researches, etc.

EXAMPLES

Hereinafter, the present invention will be described in more detail by unlimiting examples with reference to the accompanying drawings.

In the Examples, fusion proteins were prepared by: annealing chemically-synthesized forward and reverse oligonucleotides; amplifying DNA fragments through PCR reaction (Polymerase chain reaction) using the oligonucleotides; and linking the amplified DNA fragments through ligation reaction using a DNA ligase. Herein, "MWPsp" refers to a signal peptide of MWP protein; and the number following MWPmp (i.e., MWPmp1, 2, 3, ...) refers to the number of amino acids (i.e., 1, 2, 3, ... amino acids) of MWP mature protein from the N-terminus.

Example 1

Construction of Vector pPINS-1 Incorporating Fusion DNA MWPsp-MWPmp10-(His)$_6$-Linker-Met-Proinsulin (1) Preparation of DNA Fragment MWPsp-MWPmp10

The following (i) to (iv) were added in a 0.5 ml tube to give a reaction solution of 100 μl, and a PCR reaction was performed according to a known method (Innis, M. A et al., PCR Protocols, A guide to methods and applications, Academic Press, 1990) by repeating 30 cycles of: denaturation at 94° C. for 1 min.; annealing at 55° C. for 1 min.; and DNA chain elongation at 72° C. for 1 min.

(i) Template DNA 840 ng of genomic DNA which was extracted from *Bacillus brevis* (strain 47-5Q) according to a known method (Molecular Cloning 2nd ed., A Laboratory Manual, Cold Spring Harbor Laboratory (1989)).

(ii) Primers

Forward primer 5'-GTCGTTAACAGTGTATTGCT-3' (SEQ ID NO:6) and reverse primer 5'-TGGAGCTGTAGTAGTTGCTGCTTCTTCTGC-3' (SEQ ID NO:7) which were prepared by organic synthesis based on the nucleotide sequences for MWP protein determined by Yamagata, H. et al. (J. Bacteriol., 169, 1239–1245, 1987) and Tsuboi, A. et al. (J. Bacteriol., 170, 935–945, 1988): These primers were added to a final concentration of 0.1 μM.

(iii) Taq DNA Polymerase

5 U of commercially available Taq DNA polymerase (GIBCO BRL).

(iv) Others

Tris-HCl (final concentration 20 mM, pH 8), MgCl2 (final concentration 2.5 mM) and dNTPs (dATP, dGTP, dCTP and dTTP, final concentration 50 μM each).

At the end of the PCR reaction, the reaction mixture was condensed with phenol and applied to 0.8% agarose gel for electrophoresis under normal conditions. The PCR product, i.e., DNA fragment MWPsp-MWPmp10, was recovered from the agarose gel using Ultrafree C3H (Millipore Corp.). The recovered PCR product was treated with phenol, subjected to ethanol precipitation, dried in vacuum, and dissolved in a suitable amount of distilled water. Thereafter, the resultant PCR product was blunt-ended using DNA Blunting Kit (Takara Shuzo, Co., Ltd.) following the manufacturer's instruction.

(2) Preparation of DNA Fragment (His)$_6$

In accordance with the genetic code table (Molecular Cloning 2nd ed., A Laboratory Manual, Cold Spring Harbor Laboratory (1989)), the forward oligonucleotide 5'-CATCATCATCATCATCAC-3' (SEQ ID NO:8) and reverse oligonucleotide 5'-GTGATGATGATGATGATG-3' (SEQ ID NO:9) coding for (His)$_6$ were chemically synthesized. The oligonucleotides were phosphorylated using T4 polynucleotide kinase (Nippon Gene) following the manufacturer's instruction, treated in a solution of 10 mM Tris-HCl (pH 8) and 5 mM MgCl$_2$ at 95° C. for 5 min., and annealed at 37° C. for 15 min. The annealed double-stranded DNA fragment (His)$_6$ was treated with phenol, subjected to ethanol precipitation, dried in vacuum, and dissolved in a suitable amount of distilled water.

(3) Preparation of DNA Fragment Linker

In accordance with the genetic code table (supra), the forward oligonucleotide 5'-GGTTCTCCAGTACCTTCTGGA-3' (SEQ ID NO:53) and reverse oligonucleotide 5'-TCCAGAAGGTACTGGAGAACC-3' (SEQ ID NO:10) coding for Linker Gly Ser Pro Val Pro Ser Gly (SEQ ID NO:1) were chemically synthesized and were annealed as described in (2) of the present example to obtain a double-stranded DNA fragment Linker.

(4) Preparation of DNA Fragment Proinsulin

A blunt-ended DNA fragment Proinsulin was prepared in the same manner as described in (1) of the present example except that:

(a) 10 ng of a plasmid vector incorporating human proinsulin DNA was used as template DNA, which vector was prepared by: synthesizing human pancreatic cDNA from commercially available human pancreatic mRNA (Clontech) using 1st strand cDNA synthesis kit (Pharmacia) following the manufacturer's instruction; synthesizing forward primer 5'-ATGGCCCTGTGGATGCGCC-3' (SEQ ID NO:1) and reverse primer 5'-CTAGTTGCAGTAGTTCTCC-3' (SEQ ID NO:12) based on the nucleotide sequence of the human proinsulin gene determined by Bell, G. I. et al. (Nature, 282, 525–527, 1979); conducting a PCR reaction using the above-obtained cDNA as template and the synthesized oligonucleotides by repeating 35 cycles of treatments at 94° C. for 1 min., 60° C. for 1 min. and 72° C. for 1 min; and cloning the thus-obtained PCR product, i.e., human proinsulin DNA, into pGEM-T vector (Promega);

(b) forward primer 5'-TTTGTGAACCAACACCTG-3' (SEQ ID NO:13) and reverse primer 5'-CTAGTTGCAGTAGTTCTCC-3' (SEQ ID NO:12) were used; and (c) the PCR reaction was conducted by repeating 25 cycles of: denaturation at 94° C. for 1 min.; annealing at 53° C. for 1 min.; and DNA chain elongation at 72° C. for 30 sec.

(5) Preparation of DNA Fragment Met-Proinsulin

A blunt-ended DNA fragment Met-Proinsulin was prepared in the same manner as described in (4) of the present example except that: (a) 10 ng of the PCR product Proinsulin obtained in (4) of the present example was used as template DNA; and (b) forward primer 5'-ATGTTTGTGAACCAACACCTG-3' (SEQ ID NO:54) was used.

The blunt-ended DNA fragment Met-Proinsulin was further subjected to a phosphorylation reaction using T4 polynucleotide kinase (Nippon Gene) following the manufacturer's instruction, thereby obtaining phosphorylated DNA fragment Met-Proinsulin.

(6) Preparation of Fusion DNA MWPsp-MWPmp10-(His)6

A blunt-ended fusion DNA MWPsp-MWPmp10-(His)$_6$ was prepared in the same manner as described in (1) of the present example except that: (a) template DNA was prepared by reacting a suitable amount of the DNA fragment MWPsp-MWPmp10 obtained in (1) of the present example with a suitable amount of the DNA fragment (His)$_6$ obtained in (2) of the present example at 16° C. for 30 min. using DNA ligation kit (Takara Shuzo, Co., Ltd.); (b) reverse primer 5'-GTGATGATGATGATGATG-3' (SEQ ID NO:9) was used; and (c) the PCR reaction was conducted by repeating 25 cycles of: denaturation at 94° C. for 1 min.; annealing at 45° C. for 1 min.; and DNA chain elongation at 72° C. for 30 sec.

Thereafter, the obtained PCR product was phosphorylated using T4 polynucleotide kinase (Nippon Gene) following the manufacturer's instruction. The phosphorylated PCR product was introduced into a HincII-cut vector (Blue Script SK-, Stratagene) using DNA ligation kit (Takara Shuzo, Co., Ltd.) to transform *E. coli* DH5α according to a known method (Molecular Cloning 2nd ed., A Laboratory Manual, Cold Spring Harbor Laboratory (1989)). The plasmid vector DNA was purified from the transformant. To confirm that MWPsp-MWPmp10-(His)$_6$ fusion DNA was obtained, the nucleotide sequence of the vector was determined using the forward or reverse primer for sequencing the vector (i.e., M13 forward or reverse primer). A second PCR reaction was conducted in the same manner as described above, using the vector incorporating MWPsp-MWPmp10-(His)$_6$ as template DNA, and forward primer 5'-GTCGTTAACAGTGTATTGCT-3' (SEQ ID NO:6) and reverse primer 5'-GTGATGATGATGATGATG-3' (SEQ ID NO:9), thereby preparing blunt-ended fusion DNA MWPsp-MWPmp10-(His)$_6$.

(7) Preparation of Fusion DNA MWPsp-MWPmp10-(His)$_6$-Linker

A blunt-ended fusion DNA MWPsp-MWPmp10-(His)$_6$-Linker was prepared in the same manner as described in (6) of the present example except that: (a) template DNA for the first PCR reaction was prepared by reacting a suitable amount of the fusion DNA MWPsp-MWPmp10-(His)$_6$ obtained in (6) above with a suitable amount of the DNA fragment Linker obtained in (3) above at 16° C. for 30 min. using DNA ligation kit (Takara Shuzo, Co., Ltd.); and (b) reverse primer 5'-TCCAGAAGGTACTGGAGAACC-3' (SEQ ID NO:10) was used for the first PCR reaction.

(8) Preparation of Vector Incorporating Fusion DNA MWPsp-MWPmp10-(His)$_6$-Linker-Met-Proinsulin Vector pPINS-1 incorporating fusion product MWPsp-MWPmp10-(His)6-Linker-Met-Proinsulin was prepared in the same manner as described in (6) of the present example except that: (a) template DNA for the first PCR reaction was prepared by reacting a suitable amount of the fusion DNA MWPsp-MWPmp10-(His)$_6$-Linker obtained in (7) of the present example with a suitable amount of the DNA fragment Met-Proinsulin obtained in (5) of the present example at 16° C. for 30 min. using DNA ligation kit (Takara Shuzo, Co., Ltd.); and (b) reverse primer 5'-CTAGTTGCAGTAGTTCTCC-3' (SEQ ID NO:12) was used for the first PCR reaction.

Example 2

Construction of Vectors Respectively Incorporating Fusion DNAs MWPsp-MWPmp6-, 8-, 9-, 11-, 12-, 15-, 40-, 50-, 100-(His)$_6$-Linker-Met-Proinsulin (1) Preparation of DNA Fragments MWPsp-MWPmp6, 8, 9, 11, 12, 15, 40, 50, 100

DNA fragments MWPsp-MWPmp6, 8, 9, 11, 12, 15, 40, 50, 100 were prepared in the same manner as described in (1) of Example 1 except that:

(a) the following primers were used as the reverse primers:

|  |  |  |
|---|---|---|
| MWPmp6: | 5'-AGTTGCTGCTTCTTCTGC-3' | (SEQ ID NO:14) |
| MWPmp8: | 5'-TGTAGTAGTTGCTGCTTC-3' | (SEQ ID NO:15) |
| MWPmp9: | 5'-AGCTGTAGTAGTTGCTGC-3' | (SEQ ID NO:16) |
| MWPmp11: | 5'-TTTTGGAGCTGTAGTAGT-3' | (SEQ ID NO:17) |
| MWPmp12: | 5'-CATTTTTGGACCTGTAGT-3' | (SEQ ID NO:18) |
| NWPmp15: | 5'-ATCAGCGTCCATTTTTGG-3' | (SEQ ID NO:19) |
| MWPmp40: | 5'-GTCTACACCGTATTCGCCGT-3' | (SEQ ID NO:20) |
| MWPmp50: | 5'-AGTAGCGAACTCTGCACGAG-3' | (SEQ ID NO:21) |
| MWPmp100: | 5'-AGATTTGTCCGGGAAACCTT-3' | (SEQ ID NO:22) | and (b) the PCR reaction was conducted by repeating 30 cycles of: denaturation at 94° C. for 1 min.; annealing at 45° C. for 1 min.; and DNA chain elongation at 72° C. for 1 min.

(2) Preparation of DNA Fragment (His)$_6$-Linker-Met-Proinsulin

A blunt-ended DNA fragment (His)$_6$-Linker-Met-Proinsulin was prepared in the same manner as described in (1) of Example 1 except that: (a) 10 ng of the vector pPINS-1 incorporating the fusion DNA MWPsp-MWPmp10-(His)$_6$-Linker obtained in (8) of Example 1 was used as template DNA; (b) forward primer 5'-CATCATCATCATCATCAC-3' (SEQ ID NO:8) and reverse primer 5'-CTAGTTGCAGTAGTTCTC-3' (SEQ ID NO:23) were used; and (c) the PCR reaction was conducted by repeating 25 cycles of: denaturation at 94° C. for 1 min.; annealing at 47° C. for 1 min.; and DNA chain elongation at 72° C. for 30 sec.

The blunt-ended DNA fragment (His)$_6$-Linker-Met-Proinsulin was further subjected to a phosphorylation reaction using T4 polynucleotide kinase (Nippon Gene) following the manufacturer's instruction, thereby obtaining phosphorylated DNA fragment (His)$_6$-Linker-Met-Proinsulin.

(3) Preparation of Vectors Respectively Incorporating Fusion DNAs MWPsp-MWPmp6-, 8-, 9-, 11-, 12-, 15-, 40-, 50-, 100-(His)$_6$-Linker-Met-Proinsulin Vectors respectively incorporating fusion DNAs MWPsp-MWPmp6-, 8-, 9-, 11-, 12-, 15-, 40-, 50-, 100-(His)$_6$-Linker-Met-Proinsulins were prepared as described in (8) of Example 1 except that template DNA for the first PCR reaction was prepared by reacting a suitable amount of the respective DNA fragments MWPsp-MWPmp6, 8-, 9-, 11-, 12-, 15-, 40-, 50-, 100 obtained in (1) of the present example with a suitable amount of the DNA fragment (His)$_6$-Linker-Met-Proinsulin obtained in (2) of the present example at 16° C. for 30 min. using DNA ligation kit (Takara Shuzo, Co., Ltd.).

Example 3

Construction of Vector pPINS-2 Incorporating Fusion DNA MWPsp-MWPmp10-Met-Proinsulin Vector pPINS-2 incorporating fusion DNA MWPsp-MWPmp10-Met-Proinsulin was prepared in the same manner as described in (8) of Example 1 except that template DNA for the first PCR reaction was prepared by reacting a suitable amount of the DNA fragment MWPsp-MWPmp10 obtained in (1) of Example 1 with a suitable amount of the DNA fragment Met-Proinsulin obtained in (5) of Example 1 at 16° C. for 30 min. using DNA ligation kit (Takara Shuzo, Co., Ltd.).

Example 4

Construction of Vectors Respectively Incorporating Fusion DNAs MWPsp-MWPmp1-, 2-, 3-, 4-, 5-, 6-, 7-, 8-, 9-, 11-, 12-, 13-, 14-, 15-, 17-, 20-, 50-Met-Proinsulin (1) Preparation of DNA Fragments MWPsp-MWPmp1, 2, 3, 4, 5, 7, 13, 14, 17, 20

Blunt-ended DNA fragments MWPsp-MWPmp1, 2, 3, 4, 5, 7, 13, 14, 17, 20 were prepared in the same manner as described in (1) of Example 1 except that:

(a) the following primers were used as the reverse primers:

```
MWPmp1:  5'-TGCTGCGAAAGCCATTGG-3'      (SEQ ID NO:24)
MWPmp2:  5'-TTCTGCTGCGAAAGCCAT-3'      (SEQ ID NO:25)
MWPmp3:  5'-TTCTTCTGCTGCGAAAGC-3'      (SEQ ID NO:26)
MWPmp4:  5'-TGCTTCTTCTGCTGCGAA-3'      (SEQ ID NO:27)
MWPmp5:  5'-TGCTGCTTCTTCTGCTGC-3'      (SEQ ID NO:28)
MWPmp7:  5'-AGTAGTTGCTGCTTCTTC-3'      (SEQ ID NO:29)
MWPmp13: 5'-GTCCATTTTTGGAGCTGT--3'     (SEQ ID NO:30)
MWPmp14: 5'-AGCGTCCATTTTTGGAGC-3'      (SEQ ID NO:31)
MWPmp17: 5'-TTCCATATCAGCGTCCAT-3'      (SEQ ID NO:32)
MWPmp20: 5'-TACGGTTTTTTCCATATCAGC-3';  (SEQ ID NO:33)
``` and (b) the PCR reaction was conducted by repeating 30 cycles of: denaturation at 94° C. for 1 min.; annealing at 45° C. for 1 min.; and DNA chain elongation at 72° C. for 1 min.

(2) Preparation of Vectors Respectively Incorporating Fusion DNAs MWPsp-MWPmp1-, 2-, 3-, 4-, 5-, 6-, 7-, 8-, 9-, 11-, 12-, 13-, 14-, 15-, 17-, 20-, 50-Met-Proinsulin Vectors respectively incorporating fusion DNAs MWPsp-MWPmp1-, 2-, 3-, 4-, 5-, 6-, 7-, 8-, 9-, 11-, 12-, 13-, 14-, 15-, 17-, 20-, 50-Met-Proinsulin were prepared in the same manner as described in (8) of Example 1 except that: (a) template DNA for the first PCR reaction was prepared by reacting a suitable amount of the respective DNA fragments MWPsp-MWPmp1-, 2-, 3-, 4-, 5-, 6-, 7-, 8-, 9-, 11-, 12-, 13-, 14-, 15-, 17-, 20-, 50 obtained in (1) of Example 2 and (1) of the present example with a suitable amount of the DNA fragment Met-Proinsulin obtained in (5) of Example 1 at 16° C. for 30 min. using DNA ligation kit (Takara Shuzo, Co., Ltd.).

Example 5

Construction of Vector Incorporating Fusion DNA MWPsp-Proinsulin (1) Preparation of DNA Fragment MWPsp A blunt-ended DNA fragment MWPsp was prepared in the same manner as described in (1) of Example 1 except that reverse primer 5'-TGCGAAAGCCATTGGAGCAAC-3' (SEQ ID NO:34) was used for the PCR reaction.

(2) Preparation of Vector Incorporating Fusion DNA MWPsp-Proinsulin

A vector incorporating MWPsp-Proinsulin fusion DNA was prepared in the same manner as described in (8) of Example 1, except that template DNA for the first PCR reaction was prepared by reacting a suitable amount of the DNA fragment MWPsp obtained in (1) of the present example with a suitable amount of the blunt-ended DNA fragment Proinsulin obtained in (4) of Example 1 at 16° C. for 30 min. using DNA ligation kit (Takara Shuzo, Co., Ltd.).

Example 6

Construction of Vectors Respectively Incorporating Fusion DNAs MWPsp-Somatostatin 28, MWPsp-MWPmp10-(His)$_6$-EGF-TEV-Somatostatin 28, MWPsp-MWPmp10-(His)$_6$-TEV-Somatostatin 28 and MWPsp-MWPmp20-(His)$_6$-EGF-TEV-Somatostatin 28 (pSTN)

(1) Preparation of DNA Fragment Somatostatin 28

A blunt-ended DNA fragment Somatostatin 28 was prepared in the same manner as described in (1) of Example 1 except that:

(a) 10 ng of human somatostatin 28 single-stranded DNA (5'-TCTGCTAACTCAAACCCGGCTATGGCACCCCGAGA-ACGCAAAGCTGGCTGCAAGAATTTCTTCTGGAAGA-CTTTCACATCCTGTTAG-3' (SEQ ID NO:55)) was prepared as template DNA by organic synthesis based on the nucleotide sequence determined by Shen, L. -P et al. (Proc. Natl. Acad. Sci. U.S.A., 79, 4575–4579, 1982);

(b) forward primer 5'-TCTGCTAACTCAAACCCG-3' (SEQ ID NO:35) and reverse primer 5'-CTAACAGGATGTGAAAGTCTT-3' (SEQ ID NO:36) were used; and (c) the PCR reaction was conducted by repeating 25 cycles of: denaturation at 94° C. for 1 min.; annealing at 50° C. for 1 min.; and DNA chain elongation at 72° C. for 10 sec.

The blunt-ended DNA fragment somatostatin 28 was further subjected to a phosphorylation reaction using T4 polynucleotide kinase (Nippon Gene) following the manufacturer's instruction, thereby obtaining phosphorylated DNA fragment somatostatin 28.

(2) Preparation of DNA Fragment EGF

A blunt-ended DNA fragment EGF was prepared in the same manner as described in (1) of Example 1 except that:

(a) 10 ng of human epidermal growth factor (EGF) single-stranded DNA (5'-AACTCTGACTCCGAATGCCCGCTGTCTCACGACGG-TTATTGCCTGCATGATGGTGTTTGTATGTATATCGAA-GCTCTGGACAAATATGCTTGCAACTGTGTTGTTGGT-TACATCGGTGAGCGTTGCCAGTATCGCGACCTGAA-ATGGTGGGAACTGCGT-3' (SEQ ID NO:56)) prepared by organic synthesis based on the nucleotide sequence for human epidermal growth factor determined by Bell, G. I. et al. (Nucleic Acids Res., 14, 8427–8446, 1986) was used as template DNA;

(b) forward primer 5'-AACTCTGACTCCGAATGC-3' (SEQ ID NO:37) and reverse primer 5'-ACGCAGTTCCCACCATTT-3' (SEQ ID NO:38) were used; and (c) the PCR reaction was conducted by repeating 25 cycles of: denaturation at 94° C. for 1 min.; annealing at 50° C. for 1 min.; and DNA chain elongation at 72° C. for 15 sec.

The blunt-ended DNA fragment EGF was further subjected to a phosphorylation reaction using T4 polynucleotide kinase (Nippon Gene) following the manufacturer's instruction, thereby obtaining phosphorylated DNA fragment EGF.

(3) Preparation of DNA Fragment TEV

In accordance with the genetic code table (supra), the forward oligonucleotide 5'-GACTATGATATCCCGACCACTGAAAACCTGTACT-TCCAA-3' (SEQ ID NO:57) and reverse oligonucleotide 5'-TTGGAAGTACAGGTTTTCAGTGGTCGGGATATCA-TAGTC-3' (SEQ ID NO:58) coding for an amino acid sequence recognized by TEV protease were chemically synthesized and annealed as described in (2) of Example 1, thereby obtaining a double-stranded DNA fragment TEV.

(4) Preparation of Fusion DNA MWPsp-MWPmp10-(His)$_6$-EGF

A blunt-ended fusion DNA MWPsp-MWPmp10-(His)$_6$-EGF was prepared as described in (6) of Example 1 except that: (a) template DNA for the first PCR reaction was prepared by reacting a suitable amount of the fusion DNA MWPsp-MWPmp10-(His)$_6$ obtained in (6) of Example 1 with a suitable amount of the DNA fragment EGF obtained in (2) of the present example at 16° C. for 30 min. using DNA ligation kit (Takara Shuzo, Co., Ltd.); and (b) reverse primer 5'-ACGCAGTTCCCACCATTT-3' (SEQ ID NO:38) was used for the first PCR reaction.

(5) Preparation of fusion DNA MWPsp-MWPmp10-(His)$_6$-TEV

A blunt-ended fusion DNA MWPsp-MWPmp10-(His)$_6$-TEV was prepared as described in (6) of Example 1 except that: (a) template DNA for the first PCR reaction was prepared by reacting a suitable amount of the fusion DNA MWPsp-MWPmp10-(His)$_6$ obtained in (6) of Example 1 with a suitable amount of the DNA fragment TEV obtained in (3) of the present example at 16° C. for 30 min. using DNA ligation kit (Takara Shuzo, Co., Ltd.); and (b) reverse primer 5'-TTGGAAGTACAGGTTTTC-3' (SEQ ID NO:39) was used for the first PCR reaction.

(6) Preparation of Fusion DNA MWPsp-MWPmp10-(His)$_6$-EGF-TEV

A blunt-ended fusion DNA MWPsp-MWPmp10-(His)$_6$-EGF-TEV was prepared in the same manner as described in (6) of Example 1 except that: (a) template DNA for the first PCR reaction was prepared by reacting a suitable amount of the fusion DNA MWPsp-MWPmp10-(His)$_6$-EGF obtained in (4) of the present example with a suitable amount of the DNA fragment TEV obtained in (3) of the present example at 16° C. for 30 min. using DNA ligation kit (Takara Shuzo, Co., Ltd.); and (b) reverse primer 5'-TTGGAAGTACAGGTTTTC-3' (SEQ ID NO:39) was used for the first PCR reaction.

(7) Preparation of Fusion DNA MWPsp-MWPmp20-(His)$_6$

A blunt-ended fusion DNA MWPsp-MWPmp20-(His)$_6$ was prepared in the same manner as described in (6) of Example 1, except that template DNA for the first PCR reaction was prepared by reacting a suitable amount of the DNA fragment MWPsp-MWPmp20 obtained in (1) of Example 4 with a suitable amount of the DNA fragment (His)$_6$ obtained in (2) of Example 1 at 16° C. for 30 min. using DNA ligation kit (Takara Shuzo, Co., Ltd.).

(8) Preparation of Fusion DNA MWPsp-MWPmp20-(His)$_6$-EGF

A blunt-ended fusion DNA MWPsp-MWPmp20-(His)$_6$-EGF was prepared in the same manner as described in (6) of Example 1 except that: (a) template DNA for the first PCR reaction was prepared by reacting a suitable amount of the fusion DNA MWPsp-MWPmp20-(His)$_6$ obtained in (7) of the present example with a suitable amount of the DNA fragment EGF obtained in (2) of the present example at 16° C. for 30 min. using DNA ligation kit (Takara Shuzo, Co., Ltd.); and (b) reverse primer 5'-ACGCAGTTCCCACCATTT-3' (SEQ ID NO:38) was used for the first PCR reaction.

(9) Preparation of Fusion DNA MWPsp-MWPmp20-(His)$_6$-EGF-TEV

A blunt-ended fusion DNA MWPsp-MWPmp20-(His)$_6$-EGF-TEV was prepared in the same manner as described in (6) of Example 1 except that: (a) template DNA for the first PCR reaction was prepared by reacting a suitable amount of the fusion DNA MWPsp-MWPmp20-(His)$_6$-EGF obtained in (8) of the present example with a suitable amount of the DNA fragment TEV obtained in (3) of the present example at 16° C. for 30 min. using DNA ligation kit (Takara Shuzo, Co., Ltd.); and (b) reverse primer 5'-TTGGAAGTACAGGTTTTC-3' (SEQ ID NO:39) was used for the first PCR reaction.

(10) Preparation of Vectors Respectively incorporating fusion DNAs MWPsp-Somatostatin 28, MWPsp-MWPmp10- (His)$_6$-EGF-TEV-Somatostatin 28, MWPsp-MWPmp10-(His)$_6$-TEV-Somatostatin 28 and MWPsp-MWPmp20-(His)$_6$-EGF-TEV-Somatostatin 28

Vectors respectively incorporating fusion DNAs MWPsp-Somatostatin 28, MWPsp-MWPmp10-(His)$_6$-EGF-TEV-Somatostatin 28, MWPsp-MWPmp10-(His)$_6$-TEV-Somatostatin 28 and MWPsp-MWPmp20-(His)$_6$-EGF-TEV-Somatostatin 28 were prepared in the same manner as described in (8) of Example 1 except that: (a) template DNA for the first PCR reaction for MWPsp-Somatostatin 28 was prepared by reacting the DNA fragment MWPsp obtained in (1) of Example 5 with the DNA fragment Somatostatin 28 obtained in (1) of the present example at 16° C. for 30 min. using DNA ligation kit (Takara Shuzo, Co., Ltd.), and template DNAs for the first PCR reactions for MWPsp-MWPmp10-(His)$_6$-EGF-TEV-Somatostatin 28, MWPsp-MWPmp10-(His)$_6$-TEV-Somatostatin 28 and MWPsp-MWPmp20-(His)$_6$-EGF-TEV-Somatostatin 28 were prepared by reacting a suitable amount of the DNA fragment Somatostatin 28 with a suitable amount of the respective fusion DNAs MWPsp-MWPmp10-(His)$_6$-TEV, MWPsp-MWPmp10-(His)$_6$-EGF-TEV and MWPsp-MWPmp20-(His)$_6$-EGF-TEV obtained in (5), (6) and (9) of the present example at 16° C. for 30 min. using DNA ligation kit (Takara Shuzo, Co., Ltd.); and reverse primer 5'-CTAACAGGATGTGAAAGTCTT-3' (SEQ ID NO:36) was used for the first PCR reactions.

Example 7

Construction of Vectors Respectively Incorporating Fusion DNAs MWPsp-Glucagon, MWPsp-MWPmp10-(His)$_6$-Linker-V8-Glucagon, MWPsp-MWPmp20-(His)$_6$-Linker-V8-Glucagon (pGCN) and MWPsp-MWPmp30-(His)$_6$-Linker-V8-Glucagon (1) Preparation of DNA Fragment Glucagon A blunt-ended DNA fragment Glucagon was prepared in the same manner as described in (1) of Example 1 except that:

(a) 10 ng of human glucagon single-stranded DNA (5'-CACAGCCAAGGTACTTTCACATCCGACTACTCTAA-ATATCTGGATTCCCGTCGCGCTCAAGATTTCGTTCA-ATGGCTGATGAACACT-3' (SEQ ID NO:59)) prepared by organic synthesis based on the nucleotide sequence for human glucagon determined by Drucker, D. J. et al. (J. Biol. Chem., 263, 13475–13478, 1988) was used as template DNA;

(b) forward primer 5'-CACAGCCAAGGTACTTTC-3' (SEQ ID NO:40) and reverse primer 5'-TTAAGTGTTCATCAGCCATTG-3' (SEQ ID NO:41) were used; and (c) the PCR reaction was conducted by repeating 25 cycles of: denaturation at 94° C. for 1 min.; annealing at 50° C. for 1 min.; and DNA chain elongation at 72° C. for 10 sec.

The blunt-ended DNA fragment Glucagon was further subjected to a phosphorylation reaction using T4 polynucleotide kinase (Nippon Gene) following the manufacturer's instruction, thereby obtaining phosphorylated DNA fragment Glucagon.

(2) Preparation of DNA Fragment V8-Glucagon

A blunt-ended DNA fragment V8-Glucagon was prepared in the same manner as described in (1) of Example 1 except that:

(a) 10 ng of the human glucagon DNA obtained in (1) of the present example was used as template DNA;

(b) forward primer 5'-TTCCTGGAACACAGCCAA-3' (SEQ ID NO:42) and reverse primer 5'-TTAAGTGTTCATCAGCCATTG-3' (SEQ ID NO:41) were used; and (c) the PCR reaction was conducted by repeating 25 cycles of: denaturation at 94° C. for 1 min.; annealing at 50° C. for 1 min.; and DNA chain elongation at 72° C. for 10 sec.

The blunt-ended DNA fragment V8-Glucagon was further subjected to a phosphorylation reaction using T4 polynucleotide kinase (Nippon Gene) following the manufacturer's instruction, thereby obtaining phosphorylated DNA fragment V8-Glucagon.

(3) Preparation of DNA Fragment MWPsp-MWPmp30

A blunt-ended DNA fragment MWPsp-MWPmp30 was prepared in the same manner as described in (1) of Example 1 except that reverse primer 5'-TGCTACCAGGCCAAGAGCTT-3' (SEQ ID NO:43) was used.

(4) Preparation of Fusion DNA MWPsp-MWPmp30-(His)$_6$

A blunt-ended fusion DNA MWPsp-MWPmp30-(His)$_6$ was prepared in the same manner as described in (6) of Example 1, except that template DNA for the first PCR reaction was prepared by reacting a suitable amount of the DNA fragment MWPsp-MWPmp30 obtained in (3) of the present example with a suitable amount of the DNA fragment (His)$_6$ obtained in (2) of Example 1 at 16° C. for 30 min. using DNA ligation kit (Takara Shuzo, Co., Ltd.).

(5) Preparation of Fusion DNAs MWPsp-MWPmp20-, 30-(His)$_6$-Linker

Blunt-ended fusion DNAs MWPsp-MWPmp20-, 30-(His)$_6$-Linker were prepared in the same manner as described in (6) of Example 1 except that: (a) template DNA for the first PCR reaction was prepared by reacting a suitable amount of the DNA fragment Linker obtained in (3) of Example 1 with a suitable amount of the respective fusion DNA MWPsp-MWPmp20-(His)$_6$ and MWPsp-MWPmp30-(His)$_6$ obtained in (7) of Example 6 and (4) of the present example at 16° C. for 30 min. using DNA ligation kit (Takara Shuzo, Co., Ltd.); and (b) reverse primer 5'-TCCAGAAGGTACTGGAGAACC-3' (SEQ ID NO:10) was used for the first PCR reaction.

(6) Preparation of Vectors Respectively Incorporating Fusion DNAs MWPsp-Glucagon and MWPsp-MWPmp10-, 20-, 30- (His)$_6$-Linker-V8-Glucagon Vectors respectively incorporating fusion DNAs MWPsp-Glucagon and MWPsp-MWPmp10-, 20-, 30- (His)$_6$-Linker-V8-Glucagon were prepared in the same manner as described in (8) of Example 1 except that: (a) template DNA for the first PCR reaction for MWPsp-Glucagon was prepared by reacting a suitable amount of the DNA fragment MWPsp obtained in (1) of Example 5 with a suitable amount of the DNA fragment Glucagon obtained in (1) of the present example at 16° C. for 30 min. using DNA ligation kit (Takara Shuzo, Co. Ltd), and template DNAs for the first PCR reactions for MWPsp-MWPmp10-, 20-, 30-(His)$_6$-Linker-V8-Glucagon were prepared by reacting a suitable amount of the DNA fragment V8-Glucagon obtained in (2) of the present example with a suitable amount of the respective fusion DNAs MWPsp-MWPmp10-(His)$_6$-Linker and MWPsp-MWPmp20-, 30-(His)$_6$-Linker obtained in (7) of Example 1 and (5) of the present example at 16° C. for 30 min. using DNA ligation kit (Takara Shuzo, Co., Ltd.); and (b) reverse primer 5'-TTAAGTGTTCATCAGCCATTG-3' (SEQ ID NO:41) was used for the first PCR reactions.

Example 8

Expression/Secretion of the Fusion DNAs and Selective Cleavage of the Products (1) Amino Acid Sequences of the Fusion Products and Nucleotide Sequences Encoding the Same Among the fusion products obtained in Examples 1 to 7, the nucleotide sequences and amino acid sequences of the following products are representatively shown in SEQ ID NOS: 48–51, 62–65, and FIGS. 1 to 4.

(SEQ ID NOS:48, 62)
MWPsp-MPmp10-(His)$_6$-Linker-Met-Proinsulin (SEQ ID NOS:49, 63)
MWPsp-MWPmp10-Met-Proinsulin (SEQ ID NOS:50, 64)
MWPsp-MWPmp20-(His)$_6$-EGF-TEV-Somatostatin 28

-continued (SEQ ID NOS:51, 65)
MWPsp-MWPmp20-(His)₆-Linker-V8-Glucagon (2) Expression/Secretion of the Fusion Products The fusion proteins encoded by the fusion DNAs obtained in Examples 1 to 7 were expressed. FIG. 5 illustrates as a representative example, a manner of introducing each of the above 4 fusion DNAs into an expression vector.

Specifically, vectors (pPINS-1, pPINS-2, pSTN, pGCN) incorporating the above fusion DNAs were treated with restriction enzymes ApaLI and HindIII (when the fusion DNAs are inserted in a forward direction with respect to M13 primer for sequencing) or with ApaLI and KpnI (when the fusion DNAs are inserted in a reverse direction with respect to M13 primer for sequencing). Then, the restriction fragments were subjected to 0.8% agarose electrophoresis to cleave out DNA fragments with the fusion DNAs. A suitable amount of each of the thus-obtained fusion DNAs was reacted with a suitable amount of the *Bacillus brevis* expression vector pNU211R2L5 (JP-A-5-304962 and JP-A-7-170984) which had already been cleaved with ApaLI and HindIII (or KpnI when the fusion DNA is inserted in the reverse direction) at 16° C. for 30 min. using DNA ligation kit (Takara Shuzo, Co., Ltd.), thereby introducing each fusion DNA into the expression vector. Accordingly, expression vectors pNU-PINS-1, pNU-PINS-2, pNU-STN and pNU-GCN incorporating the respective fusion DNAs were obtained. These expression vectors were used to transform *Bacillus brevis* strain 47-5Q (FERM BP-1664) according to a known method (Methods in Enzymol., 217:23–33, 1993) whereafter the resultant transformants were grown in a T2 agar medium [polypeptone (1%), meat extract (0.5%), yeast extract (0.2%), uracil (0.1 mg/ml), glucose (1%), erythromycin (10 µg/ml), agar (1.5%), pH 7].

The transformants were each cultured in a T2 medium (removing agar from T2 agar medium) at 37° C. for 1 day. Then, plasmid DNAs were purified from each medium according to a known method (Molecular Cloning 2nd ed., A Laboratory Manual, Cold Spring Harbor Laboratory (1989)) and treated with ApaLI and HindIII (or KpnI) to confirm that the fusion DNAs were introduced into the transformants. For the transformants incorporating the fusion DNAs, expression/secretion of the fusion proteins encoded by the incorporated fusion DNAs were examined. Specifically, cell suspensions obtained from the T2 medium were individually added to a 5YC medium [polypeptone (3%), yeast extract (0.2%), glucose (3%), $CaCl_2.2H_2O$ (0.01%), $MgSO_4.7H_2O$ (0.01%), $FeSO_4.7H_2O$ (0.001%), $MnSO_4.4H_2O$ (0.001%), $ZnSO_4.7H_2O$ (0.0001%), glycin (0.3%), erythromycin (10 µg/ml), pH 7] in a volume ratio of 1:1000, which were shake cultured at 30° C. for 4 days.

At the end of cultivation, the media were centrifuged at 15,000 rpm for 2 min. to obtain supernatants for analyzing proteins by electrophoresis according to a known method (Laemmli, U. K., Nature, 227, 680–685, 1970). Specifically, 18 µl of each supernatant was added to 2 µl of Buffer 1 [125 mM Tris-HCl (pH 6.8), 20% glycerol, 4% SDS, 10% 2-mercaptoethanol], boiled for 5 min., and then added to 4 µl of Buffer 2 [250 mM Tris-HCl (pH 6.5), 50% glycerol, 0.5% BPB]. The resultant supernatants were subjected to electrophoresis using commercially available 15/25% SDS polyacrylamide gel (Daiichi Chemicals, Co. Ltd., Japan) (electrophoresis buffer: 100 mM Tris, 100 mM Tricine, 0.1% SDS) in order to determine the presence of expression/secretion of the fusion proteins by Coomassie staining.

Figure 6:
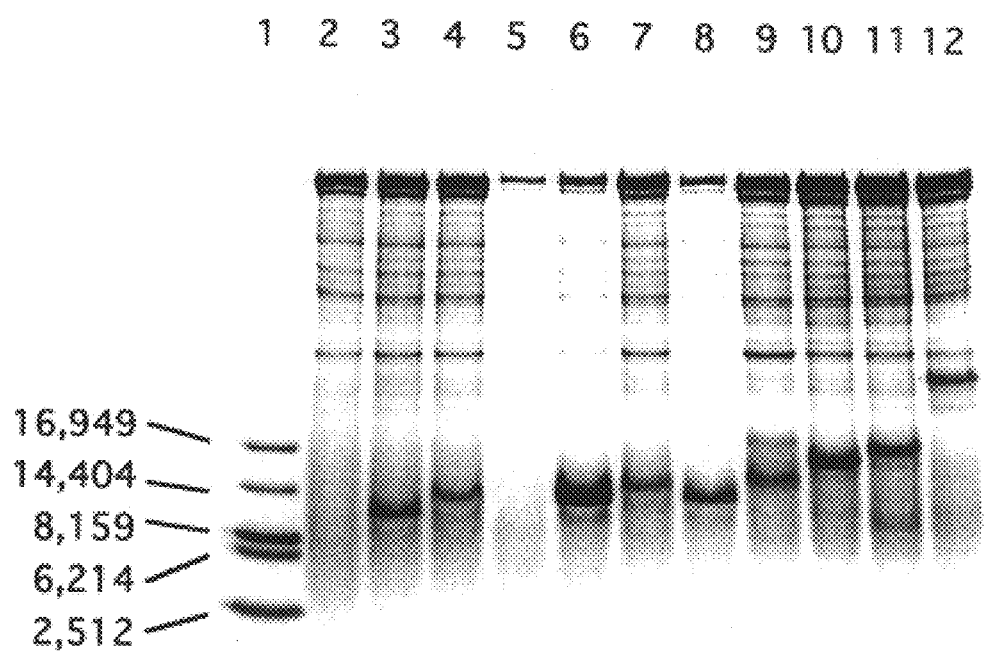
FIG. 6 is a photograph showing the results of electrophoresis of media containing proinsulin linked with His-tag produced by cultivation of the transformants: where the samples are marker peptides (lane 1), a negative control (transformed with plasmid pNU211R2L5 without gene for an exogenous protein; lane 2), and transformants MWPsp-MWPmp6-(lane 3), 8-(lane 4), 9-(lane 5), 10-(lane 6), 11-(lane 7), 12-(lane 8), 15-(lane 9), 40-(lane 10), 50-(lane 11), 100(lane 12)-(His)$_6$-Linker-Met-Proinsulin.
Figure 7:
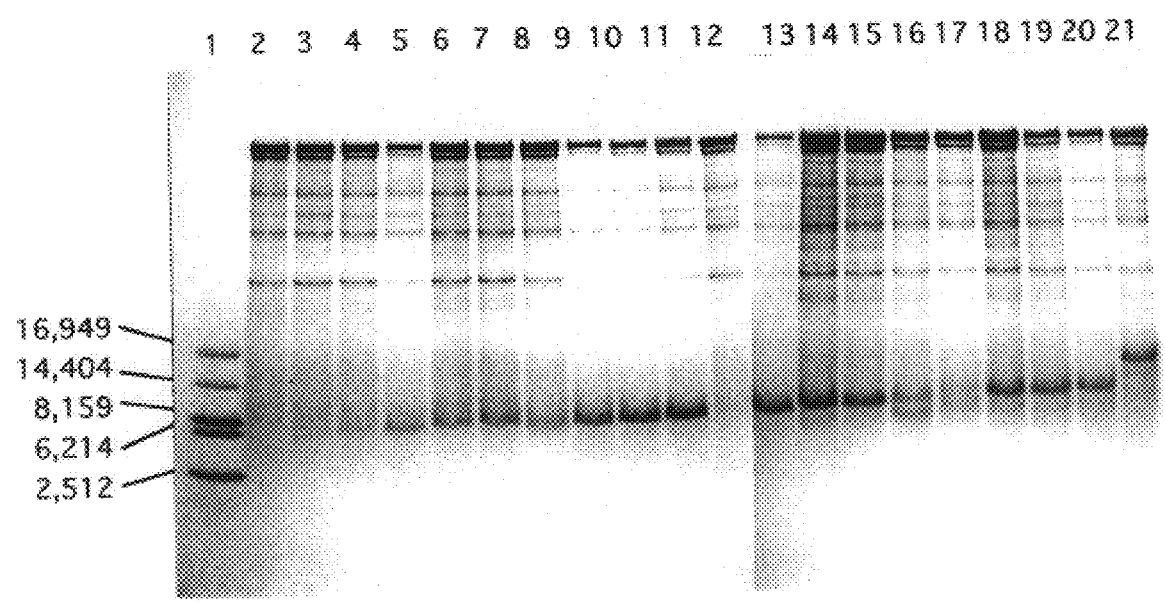
FIG. 7 is a photograph showing the results of electrophoresis of media containing proinsulin without His-tag produced by cultivation of the transformants: where the samples are marker peptides (lane 1), a negative control (transformed with plasmid pNU211R2L5 only; lane 2), transformant MWPsp-Proinsulin (lane 3), and transformants MWPsp-MWPmp1-(lane 4), 2-(lane 5), 3-(lane 6), 4-(lane 7), 5-(lane 8), 6-(lane 9), 7-(lane 10), 8-(lane 11), 9-(lane 12), 10-(lane 13), 11-(lane 14), 12-(lane 15), 13-(lane 16), 14-(lane 17), 15-(lane 18), 17-(lane 19), 20-(lane 20), 50(lane 21)-Met-Proinsulin.
Figure 8:
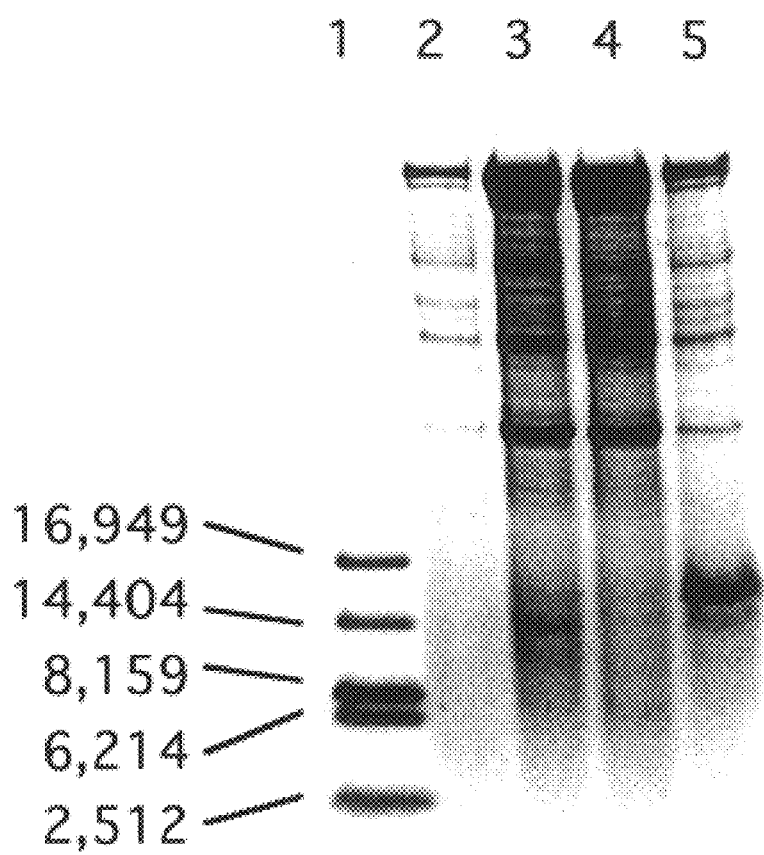
FIG. 8 is a photograph showing the results of electrophoresis of media containing somatostatin produced by cultivation of the transformants: where the samples are marker peptides (lane 1), transformant MWPsp-Somatostatin 28 (lane 2), transformant MWPsp-MWPmp10-(His)$_6$-EGF-TEV-Somatostatin 28 (lane 3), transformant MWPsp-MWPmp10-(His)$_6$-TEV-Somatostatin 28 (lane 4), and transformant MWPsp-MWPmp20-(His)$_6$-EGF-TEV-Somatostatin 28 (lane 5).
Figure 9:
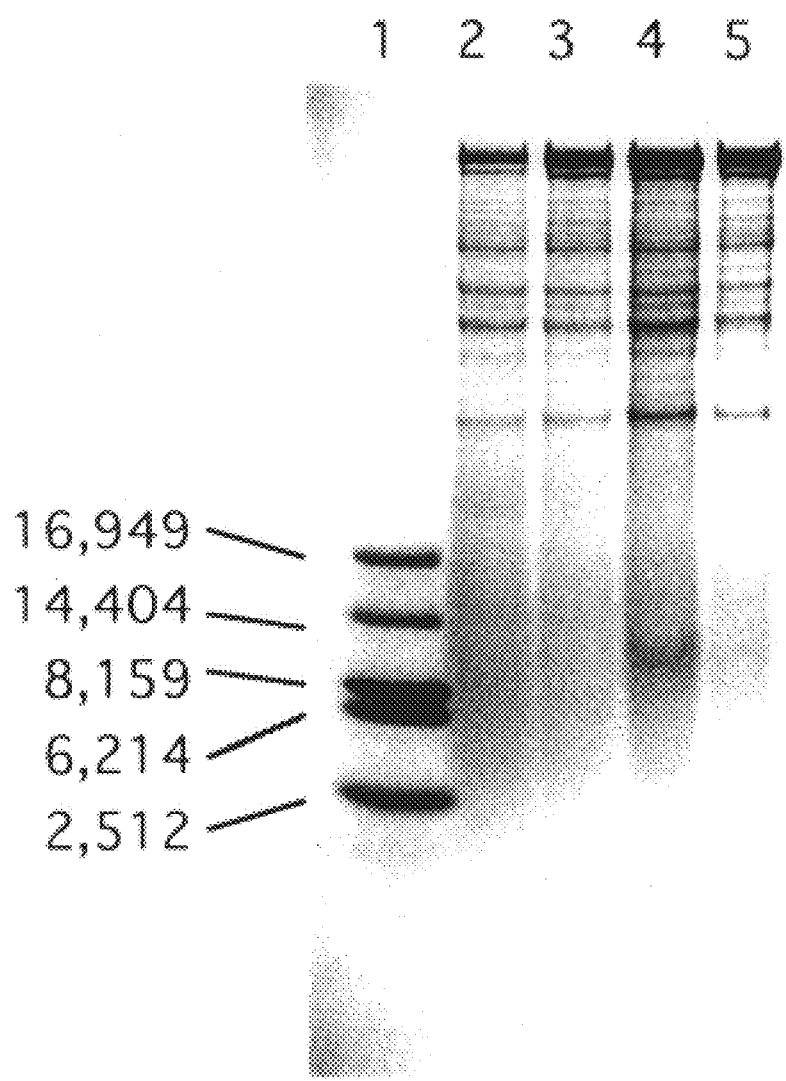
FIG. 9 is a photograph showing the results of electrophoresis of media containing glucagon produced by cultivation of the transformants: where the samples are marker peptides (lane 1), transformant MWPsp-Glucagon (lane 2), and transformants MWPsp-MWPmp10-(lane 3), 20-(lane 4), 30(lane 5)-(His)$_6$-Linker-V8-Glucagon.

The results of expression/secretion of MWPsp-MWPmp6-, 8-, 9-, 10-, 11-, 12-, 15-, 40-, 50-, 100-(His)₆-Linker-Met-Proinsulins are shown in FIG. 6 as representatives of the exogenous polypeptide proinsulin. The expression/sec-retion was observed for all of the fusion products except for MWPsp-MWPmp9-(His)₆-Linker-Met-Proinsulin (lane 5). The results of expression/secretion of MWPsp-Proinsulin, MWPsp-MWPmp1-, 2-, 3-, 4-, 5-, 6-, 7-, 8-, 9-, 10-, 11-, 12-, 13-, 14-, 15-, 17-, 20-, 50-Met-Proinsulins are shown in FIG. 7. The expression/secretion was observed for all of the fusion proteins except for MWPsp-Proinsulin (lane 3) and MWPsp-MWPmp9-Met-Proinsulin (lane 12). Higher expression/secretion levels were particularly observed for MWPsp-MWPmp6-, 7-, 8-, 10-, 11-, 12-, 15-, 17-, 20-, 50-Met-Proinsulins. The results of expression/secretion of MWPsp-Somatostatin 28, MWPsp-MWPmp10-(His)₆-EGF-TEV-Somatostatin 28, MWPsp-MWPmp10-(His)₆-TEV-Somatostatin 28 and MWPsp-MWPmp20-(His)₆-EGF-TEV-Somatostatin 28 are shown in FIG. 8 as representatives of the exogenous polypeptide somatostatin 28. Expression/secretion were not observed for MWPsp-Somatostatin 28 and MWPsp-MWPmp10-(His)₆-TEV-Somatostatin 28, but were observed for MWPsp-MWPmp10-(His)₆-EGF-TEV-Somatostatin 28 and MWPsp-MWPmp20-(His)₆-EGF-TEV-Somatostatin 28. A higher expression/secretion level was particularly observed for MWPsp-MWPmp20-(His)₆-EGF-TEV-Somatostatin 28. The results of expression/secretion of MWPsp-Glucagon and MWPsp-MWPmp10-, 20-, 30-(His)₆-Linker-V8-Glucagons are shown in FIG. 9 as representatives of the exogenous polypeptide glucagon. Expression/secretion was observed only for MWPsp-MWPmp20-(His)₆-Linker-V8-Glucagon.

(3) Identification of Proinsulin

Figure 10:
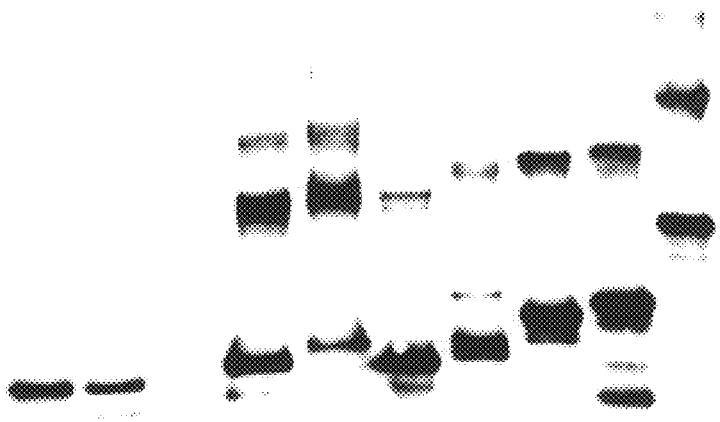
FIG. 10 is a photograph showing the results of electrophoresis/Western blotting of media containing proinsulin linked with His-tag produced by cultivation of the transformants: where the samples are a negative control (transformed with plasmid pNU211R2L5 only; lane 1), and transformants MWPsp-MWPmp6-(lane 2), 8-(lane 3), 9-(lane 4), 10-(lane 5), 11-(lane 6), 12-(lane 7), 15-(lane 8), 40-(lane 9), 50-(lane 10), 100(lane 11)-(His)$_6$-Linker-Met-Proinsulin.
Figure 11:
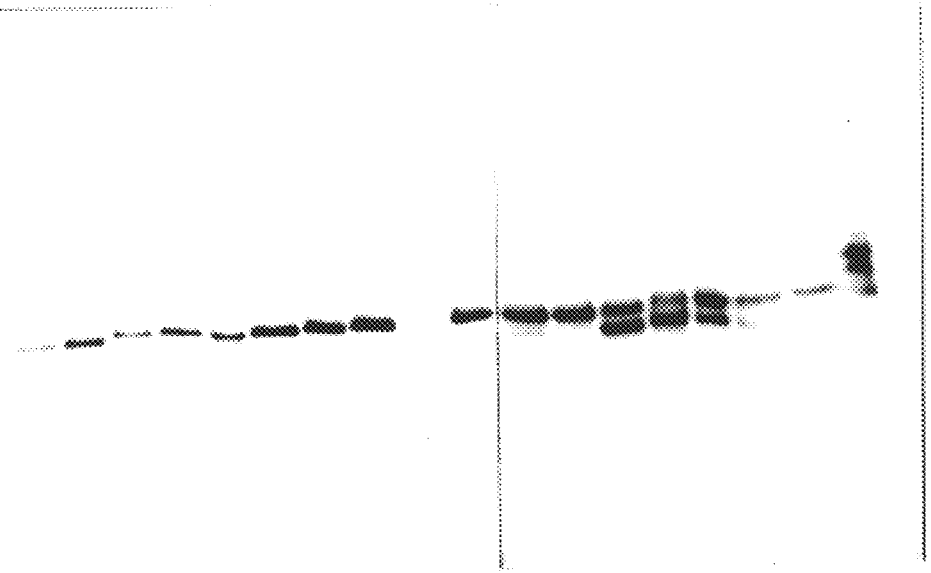
FIG. 11 is a photograph showing the results of electrophoresis/Western blotting of media containing proinsulin without His-tag produced by cultivation of the transformants: where the samples are a negative control (transformed with plasmid pNU211R2L5 only, lane 1), transformant MWPsp-Proinsulin (lane 2), and transformants MWPsp-MWPmp1-(lane 3), 2-(lane 4), 3-(lane 5), 4-(lane 6), 5-(lane 7), 6-(lane 8), 7-(lane 9), 8-(lane 10), 9-(lane 11), 10-(lane 12), 11-(lane 13), 12-(lane 14), 13-(lane 15), 14-(lane 16), 15-(lane 17), 17-(lane 18), 20-(lane 19), 50(lane 20)-Met-Proinsulin.

Proinsulin was immunologically identified using an antibody to C-peptide of proinsulin. The media were centrifuged at 15,000 rpm for 2 min. to obtain a supernatant of each medium. One µl each of the supernatants were then subjected to electrophoresis as described above and electrically blotted onto a nitrocellulose membrane according to a known method (Towbin, H. et al., 76, 4350–4354, 1979). The membrane was immersed in a solution of 5% skim milk in Buffer 3 [20 mM Tris-HCl (pH 7.4), 150 mM Nacl, 0.1% Tween 20] for 1 hour and then immersed in a rabbit anti-C-peptide antibody (LINCO RESEARCH) diluted 1:2, 000 in Buffer 3 for 30 min. under shaking condition. The membrane was then washed with Buffer 3 for 10 min. 3 times under shaking condition and immersed in a peroxidase-labeled anti-rabbit IgG antibody (E-Y Laboratories) diluted 1:2000 in Buffer 3 for 30 min. under shaking condition. After the immersion, the membrane was washed with Buffer 3 for 10 min. 3 times while shaking, in order to determine the presence of proinsulin using ECL detection kit (Amersham International plc) according to the manufacturer's instruction. As shown in FIGS. 10 and 11, signals representing the presence of proinsulin were detected for MWPsp-MWPmp6-, 8-, 10-, 11-, 12-, 15-, 40-, 50-, 100-(His)₆-Linker-Met-Proinsulins but not for pNU211R2L5 without fusion DNA and MWPsp-MWPmp9-(His)₆-Linker-Met-Proinsulin. The signals representing the presence of proinsulin were detected for MWPsp-MWPmp1-, 2-, 3-, 4-, 5-, 6-, 7-, 8-, 10-, 11-, 12-, 13-, 14-, 15-, 17-, 20-, 50-Met-Proinsulins but not for pNU211R2L5, MWPsp-Proinsulin and MWPsp-MWPmp9-Met-Proinsulin.

(4) Cleavage of Proinsulin

A transformant containing an expression vector incorporating fusion DNA MWPsp-MWPmp10-(His)₆-Linker-Met- Proinsuin was cultured in a medium. The obtained medium was centrifuged at 20,000 rpm for 15 min. To the supernatant, ammonium sulfate was added to 30% saturation. The resultant supernatant was further centrifuged at 20,000 rpm for 20 min. to obtain a pellet which was dissolved in a suitable amount of 2 mM sodium phosphate buffer (pH 7) for dialysis against the same buffer. At the end of the dialysis, the buffer of the solution was replaced with 20 mM sodium phosphate (pH 7) and 150 mM NaCl. The resultant was applied to a chelating column (Pharmacia) and eluted with the same buffer containing 300 mM imidazole to separate and purify the fusion protein from other contaminating proteins. The separated fusion protein was precipitated with ammonium sulfate and centrifuged as described above to collect the precipitate. The precipitate of the pellet was dissolved in 2 mM sodium phosphate buffer (pH 7) to dialyze against the same buffer.

Figure 12:
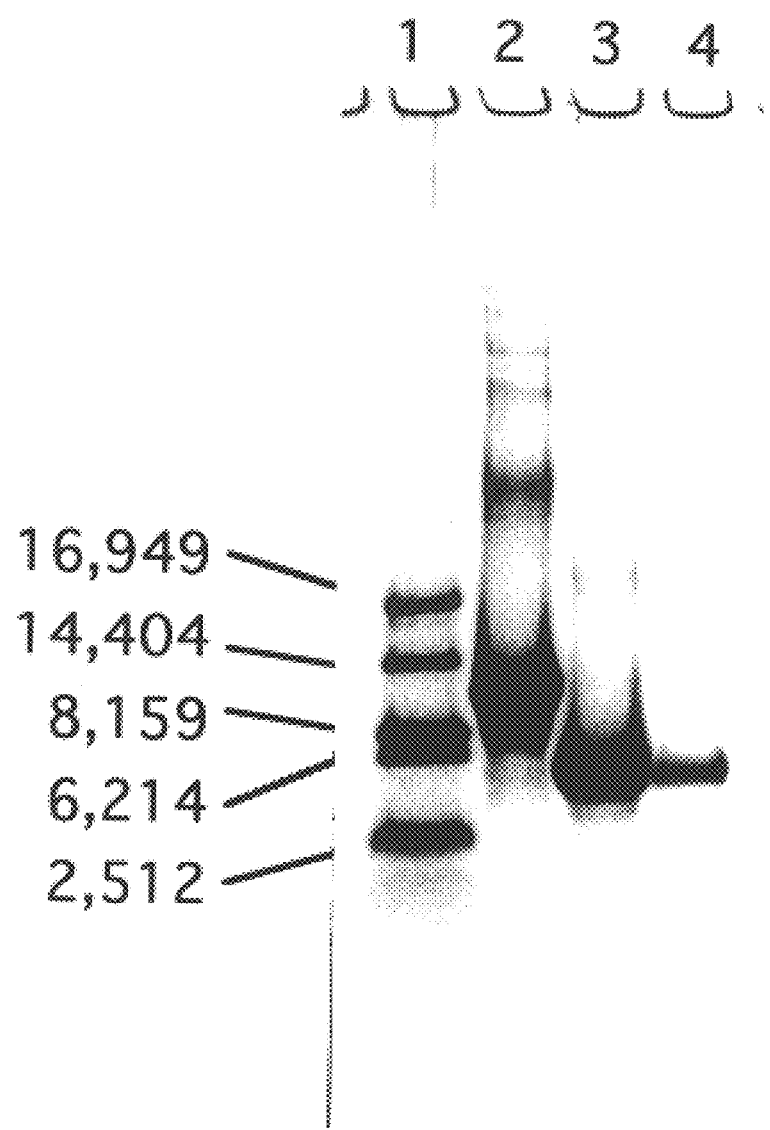
FIG. 12 is a photograph showing the results of electrophoresis of separated and purified fusion protein MWPmp10-(His)$_6$-Linker-Met-Proinsulin and proinsulin cleaved therefrom via cyanogen bromide treatment: where the samples are marker peptides (lane 1); the separated and purified fusion protein MWPmp10-(His)$_6$-Linker-Met-Proinsulin (30 µg, lane 2); the proinsulin cleaved from the fusion protein via cyanogen bromide treatment (30 µg, lane 3); and proinsulin (Sigma) (2 µg, lane 4).
Figure 13:
FIG. 13 is a photograph showing the results of electrophoresis/Western blotting of separated and purified fusion protein MWPmp10-(His)$_6$-Linker-Met-Proinsulin and proinsulin cleaved therefrom via cyanogen bromide treatment: where the samples are the separated and purified fusion protein MWPmp10-(His)$_6$-Linker-Met-Proinsulin (0.3 µg, lane 1); the proinsulin cleaved from the fusion protein via cyanogen bromide treatment (0.3 µg, lane 2); and proinsulin (Sigma) (0.3 µg, lane 3).

Then, formic acid was added to the dialyzed solution to a final concentration of 70%, to which was added cyanogen bromide in an amount corresponding to the gram equivalent of the protein. The mixture was left at room temperature overnight to chemically cleave out proinsulin from the fusion protein. The resultant was dialyzed against 2 mM sodium phosphate buffer (pH 7) and applied to a chelating column to elute proinsulin with the same buffer containing 60 mM imidazole. FIG. 12 shows the results of electrophoresis on 15/25% polyacrylamide gel and Coomassie staining of the fusion protein MWPmp10-(His)$_6$-Linker-Met-Proinsulin which was separated and purified by the chelating column but not yet cleaved, and proinsulin which had been cleaved with cyanogen bromide. FIG. 13 shows the identification of proinsulin by electrophoresis of the proteins followed by blotting on a nitrocellulose membrane using an anti-C-peptide antibody. The presence of proinsulins was confirmed for the fusion proteins.

(5) Cleavage of Somatostatin 28

Figure 14:
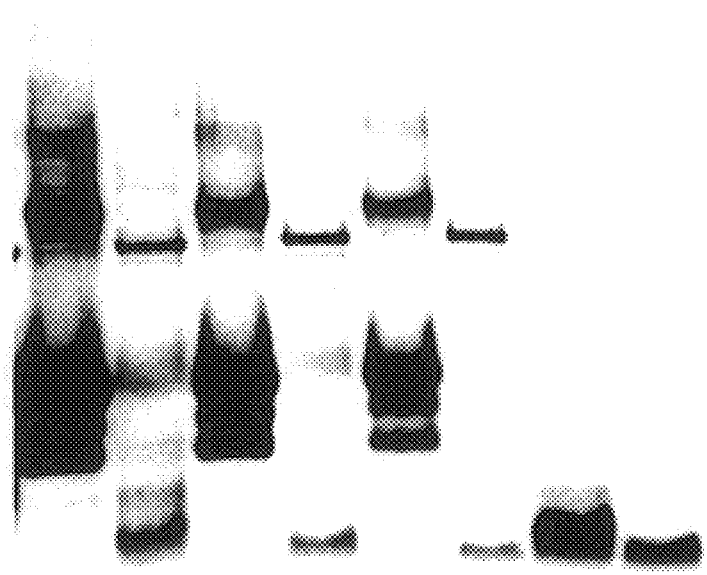
FIG. 14 is a photograph showing the results of electrophoresis/Western blotting of separated and purified fusion protein MWPmp20-(His)$_6$-EGF-TEV-Somatostatin 28 and somatostatin 28 cleaved therefrom via TEV protease treatment: where the samples are the separated and purified fusion protein MWPmp20-(His)$_6$-EGF-TEV-Somatostatin 28 (104 µg, lane 1; 52 µg, lane 3; and 26 µg, lane 5); somatostatin 28 cleaved from the fusion protein via TEV protease treatment (104 µg, lane 2; 52 µg, lane 4; and 26 µg, lane 6); and somatostatin 28 (BACHEM) (4.5 µg, lane 7; and 1.5 µg, lane 8).

The transformant containing an expression vector incorporating fusion DNA MWPsp-MWPmp20-(His)$_6$-EGF-TEV-Somatostatin 28 was cultured in a medium. The obtained medium was centrifuged at 20,000 rpm for 15 min. To the supernatant, ammonium sulfate was added to 50% saturation. The resultant supernatant was subsequently centrifuged at 20,000 rpm for 20 min. to obtain a pellet which was dissolved in a suitable amount of 2 mM sodium phosphate buffer (pH 7) for dialysis against the same buffer. At the end of the dialysis, the buffer of the solution was replaced with 20 mM sodium phosphate (pH 7) and 150 mM NaCl. The resultant was applied to a chelating column (Pharmacia) and eluted with the same buffer containing 300 mM imidazole to separate and purify the fusion protein MWPmp20-(His)$_6$-EGF-TEV-Somatostatin 28 from other contaminating proteins. The separated fusion protein of different amounts (104, 52 and 26 µg) was treated with TEV protease (GIBCO BRL, 10 U) according to the manufacturer's instruction to cleave out somatostatin 28 from the fusion protein. The protein treated with TEV protease, as well as untreated protein, was electrophoresed, blotted on a nitrocellulose membrane, and subjected to detection using a rabbit anti-somatostatin antibody (MEDAC, 2,000-fold dilution) and a peroxidase-labeled anti-rabbit IgG antibody (E-Y Laboratories, 2,000-fold dilution). FIG. 14 shows that somatostatin 28 was cleaved out with TEV protease.

(6) Cleavage of Glucagon

Figure 15:
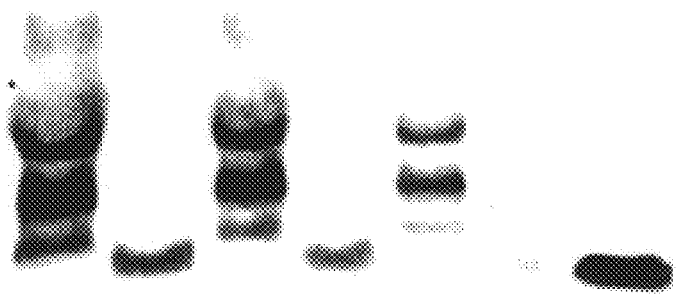
FIG. 15 is a photograph showing the results of electrophoresis/Western blotting of separated and purified fusion protein MWPmp20-(His)$_6$-Linker-V8-Glucagon and glucagon cleaved therefrom via V8 protease treatment: where the samples are the separated and purified fusion protein MWPmp20-(His)$_6$-Linker-V8-Glucagon (90 µg, lane 1; 45 µg, lane 3; and 22.5 µg, lane 5); glucagon cleaved from the fusion protein via V8 protease treatment (90 µg, lane 2; 45 µg, lane 4; and 22.5 µg, lane 6); and glucagon (Shimizu Pharmaceutical Co., Ltd., Japan) (1.5 µg, lane 7).

The transformant containing an expression vector incorporating fusion DNA MWPsp-MWPmp20-(His)$_6$-Linker-V8-Glucagon was cultured in a medium. The obtained medium was centrifuged at 20,000 rpm for 15 min. To the supernatant, ammonium sulfate was added to 50% saturation. The resultant supernatant was further centrifuged at 20,000 rpm for 20 min. to obtain a pellet which was dissolved in a suitable amount of 2 mM sodium phosphate buffer (pH 7) for dialysis against the same buffer. At the end of the dialysis, the buffer of the solution was replaced with 20 mM sodium phosphate (pH 7) and 150 mM NaCl. The resultant was applied to a chelating column (Pharmacia) and eluted with the same buffer containing 300 mM imidazole to separate and purify the fusion protein MWPmp20-(His)$_6$-Linker-V8-Glucagon from other contaminating proteins. The purified fusion protein of different amounts (90, 45 and 22.5 µg) were treated with V8 protease (Wako Pure Chemical Industries, Ltd., 2 µg) in 0.1 M ammonium carbonate to cleave out glucagon from the fusion proteins. The proteins treated and untreated with V8 protease were electrophoresed, blotted on a nitrocellulose membrane, and subjected to detection using a rabbit anti-glucagon antibody (SANBIO, 2,000-fold dilution) and a peroxidase-labeled anti-rabbit IgG antibody (E-Y Laboratories, 2,000-fold dilution). FIG. 15 shows that glucagon was cleaved out with V8 protease.

(7) Amino Acid Analysis of Proinsulin

The proinsulin cleaved from the fusion protein MWPmp10-(His)$_6$-Linker-Met-Proinsulin was identified by amino acid analysis. Specifically, the analysis was conducted by treating the fusion protein with cyanogen bromide and hydrolyzing the proinsulin which had been separated and purified by chelating column, in 6N-Hcl (containing 0.1% phenol) at 110° C. for 20 hours, before analyzing on Hitachi Amino Acid Analyzer L-8500 (Hitachi, Ltd.). As shown in Table 1 below, the amino acid composition of the proinsulin from the fusion protein was substantially consistent with the theoretical amino acid composition of natural proinsulin.

TABLE 1

| Amino acid | Theoretical value | Determined value (nmol) | Amino acid composition |
|---|---|---|---|
| A | 4 | 3.374 | 4.80 |
| R | 4 | 2.977 | 4.24 |
| N + D | 4 | 3.083 | 4.39 |
| C | 6 | 1.253 | 1.78 |
| Q + E | 15 | 10.634 | 15.13 |
| G | 11 | 8.173 | 11.63 |
| H | 2 | 1.584 | 2.25 |
| I | 2 | 1.212 | 1.72 |
| L | 12 | 8.709 | 12.39 |
| K | 2 | 1.602 | 2.28 |
| F | 3 | 2.304 | 3.28 |
| P | 3 | 3.094 | 4.40 |
| S | 5 | 2.541 | 3.62 |
| T | 3 | 2.211 | 3.15 |
| Y | 4 | 2.805 | 3.99 |
| V | 5 | 4.178 | 5.95 |
| | 85 | 59.734 | 85.00 |

(8) Estimation of Amount of Production

Figure 16:
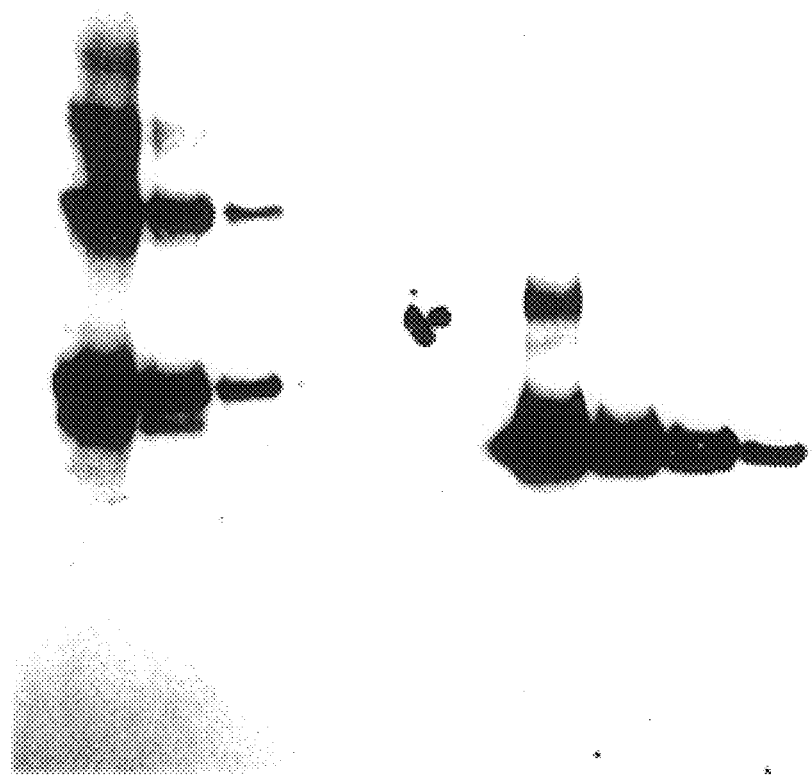
FIG. 16 is a photograph showing the results of electrophoresis/Western blotting for estimating an amount of production of fusion protein MWPmp10-(His)$_6$-Linker-Met-Proinsulin: where the samples are media obtained by cultivation of the transformant MWPmp10-(His)6-Linker-Met-Proinsulin (1 µl, lane 1; ⅓ µl, lane 2; ⅓$^2$µl, lane 3; ⅓$^3$ µl lane 4; ⅓$^4$ µl, lane 5), and proinsulin (Sigma) (1 µl, lane 6; 0.3 µl, lane 7; 0.1 µl, lane 8; 0.03 µl, lane 9; 0.01 µl, lane 10).

The fusion product MWPsp-MWPmp10-(His)$_6$-Linker-Met-Proinsulin was chosen as an example in order to estimate an amount of production thereof in a medium, by Western blotting. One µl of the supernatant obtained by 2-min. centrifugation at 15,000 rpm and 1 µl of proinsulin (Sigma) were separately subjected to serial 3″-fold dilutions, electrophoresed, and blotted on a nitrocellulose membrane to compare signal intensities detected with the anti-C peptide antibody. As shown in FIG. 16, the signal intensity of the supernatant of 3-fold dilution seemed to be comparable with that of proinsulin from 0.03 µg to 0.1 µg. Thus, the amount of production of MWPmp10-(His)$_6$-Linker-Met-Proinsulin was deduced to be in the range of 100 to 300 mg/l.

Example 9

Construction of Vector (PG-GH) Incorporating Fusion DNA MWPsp-MWPmp20-TEV-G-GH (1) Preparation of DNA Fragment MWPsp-MWPmp20

A blunt-ended DNA fragment MWPsp-MWPmp20 was prepared in the same manner as described in (1) of Example 4 except that the PCR reaction was conducted by repeating 30 cycles of: denaturation at 94° C. for 1 min.; annealing at 53° C. for 1 min.; and DNA chain elongation at 72° C. for 1 min.

(2) Preparation of DNA Fragment TEV

In accordance with the genetic code table (supra), forward oligonucleotide 5'-GACTATGATATCCCGACCACTGAAAACCTGTACT-TCCAA-3' (SEQ ID NO:57) and reverse oligonucleotide 5'-TTGGAAGTACAGGTTTTCAGTGGTCGGGATATCA-TAGTC-3' (SEQ ID NO:58) coding for an amino acid sequence (AspTyrAspIleProThrThrGluAsnLeuTyrPheGln (SEQ ID NO:2)) recognized by TEV protease were chemically synthesized. Then, the oligonucleotides were phosphorylated using T4 polynucleotide kinase (Nippon Gene) according to the manufacturer's instruction, treated in a solution of 10 mM Tris-HCl (pH 8) and 5 mM MgCl$_2$ at 95° C. for 5 min., and annealed at 37° C. for 15 min. The annealed double-stranded DNA fragment TEV was treated with phenol, subjected to ethanol precipitation, dried in vacuum and dissolved in a suitable amount of distilled water.

(3) Preparation of DNA Fragment Human Growth Hormone GH

A blunt-ended DNA fragment GH was prepared in the same manner as described in (1) of the present example except that:

(a) a plasmid vector incorporating DNA fragment GH was used as template DNA, which vector was prepared by: synthesizing human hypophysis cDNA from commercially available human hypophysis mRNA (Clontech) using 1st strand cDNA synthesis kit (Pharmacia) according to the manufacturer's instruction; synthesizing forward primer 5'-ATGGCTACAGGCTCCCGGAC-3' (SEQ ID NO:44) and reverse primer 5'-CTAGAAGCCACAGCTGCCCT-3' (SEQ ID NO:45) based on the nucleotide sequences of human growth hormone gene determined by Roskam, W. G. et al. (Nucleic Acids Res., 7, 305–320, 1979) and Martial, J. A. et al. (Science, 205, 602–607, 1979); conducting a PCR reaction using the above-obtained cDNA as template and the synthesized oligonucleotides by repeating 35 cycles of treatments at 94° C. for 1 min., 55° C. for 1 min. and 72° C. for 1 min.; and cloning the thus-obtained PCR product, i.e., human growth hormone DNA, into pGEM-T vector (Promega);

(b) forward primer 5'-TTCCCAACCATTCCCTTATC-3' (SEQ ID NO:46) and reverse primer 5'-CTAGAAGCCACAGCTGCCCT-3' (SEQ ID NO:45); and (c) the PCR reaction was conducted by repeating 25 cycles of: denaturation at 94° C. for 1 min.; annealing at 55° C. for 1 min.; and DNA chain elongation at 72° C. for 30 sec.

(4) Preparation of DNA Fragment Mutant Human Growth Hormone Linked with Gly at the N-terminus (G-GH)

A blunt-ended DNA fragment G-GH was prepared in the same manner as described in (1) of the present example except that: (a) 10 ng of the PCR product GH obtained in (3) of the present example was used as template DNA; (b) forward primer 5'-GGTTTCCCAACCATTCCCTTATC-3' (SEQ ID NO:47) and reverse primer 5'-CTAGAAGCCACAGCTGCCCT-3' (SEQ ID NO:45) were used; and (c) the PCR reaction was conducted by repeating 25 cycles of: denaturation at 94° C. for 1 min.; annealing at 55° C. for 1 min.; and DNA chain elongation at 72° C. for 30 sec.

The blunt-ended DNA fragment G-GH was then subjected to a phosphorylation reaction using T4 polynucleotide kinase (Nippon Gene) following the manufacturer's instruction, thereby obtaining phosphorylated DNA fragment G-GH.

(5) Preparation of Fusion DNA MWPsp-MWPmp20-TEV

A blunt-ended fusion DNA MWPsp-MWPmp20-TEV was prepared in the same manner as described in (1) of the present example except that: (a) template DNA for the first PCR reaction was prepared by reacting a suitable amount of the DNA fragment MWPsp-MWPmp20 obtained in (1) of the present example with a suitable amount of the DNA fragment TEV obtained in (2) of the present example at 16° C. for 30 min. using DNA ligation kit (Takara Shuzo, Co., Ltd.); (b) reverse primer 5'-TTGGAAGTACAGGTTTTC-3' (SEQ ID NO:39) was used for the first PCR reaction; and (c) the first PCR reaction was conducted by repeating 25 cycles of: denaturation at 94° C. for 1 min.; annealing at 45° C. for 1 min.; and DNA chain elongation at 72° C. for 30 sec.

Thereafter, the obtained PCR product was phosphorylated using T4 polynucleotide kinase (Nippon Gene) following the manufacturer's instruction. The phosphorylated PCR product was introduced into a HincII-cut vector (Blue Script SK-, Stratagene) using DNA ligation kit (Takara Shuzo, Co., Ltd.) in order to transform *E. coli* DH5α according to a known method (Molecular Cloning 2nd ed., A Laboratory Manual, Cold Spring Harbor Laboratory (1989)). The plasmid vector DNA was purified from the transformant. To confirm that MWPsp-MWPmp20-TEV fusion DNA was obtained, the nucleotide sequence of the vector was determined using the forward or reverse primer for sequencing the vector (i.e., M13 forward or reverse primer). A second PCR reaction was conducted in the same manner as described above, using the vector incorporating MWPsp-MWPmp20-TEV as template DNA, and forward primer 5'-GTCGTTAACAGTGTATTGCT-3' (SEQ ID NO:6) and reverse primer 5'-TTGGAAGTACAGGTTTTC-3' (SEQ ID NO:39), thereby preparing blunt-ended fusion DNA MWPsp-MWPmp20-TEV.

(6) Preparation of Vector Incorporating Fusion DNA MWPsp-MWPmp20-TEV-G-GH

Vector pG-GH incorporating fusion DNA MWPsp-MWPmp20-TEV-G-GH were prepared in the same manner as described in (5) of the present example except that: (a) template DNA was prepared by reacting a suitable amount of the fusion DNA MWPsp-MWPmp20-TEV obtained in (5) of the present example with a suitable amount of the DNA fragment G-GH obtained in (4) of the present example at 16° C. for 30 min. using DNA ligation kit (Takara Shuzo, Co., Ltd.); (b) forward primer 5'-GTCGTTAACAGTGTATTGCT-3' (SEQ ID NO:6) and reverse primer 5'-CTAGAAGCCACAGCTGCCCT-3' (SEQ ID NO:45) were used; and the PCR reaction was conducted by repeating 25 cycles of: denaturation at 94° C. for 1 min.; annealing at 53° C. for 1 min.; and DNA chain elongation at 72° C. for 1 min.

Example 10

Construction of Vector Incorporating Fusion DNA MWPsp-GH (1) Preparation of DNA Fragment MWPsp A blunt-ended DNA fragment MWPsp was prepared in the same manner as described in (1) of Example 1 except that: (a) reverse primer 5'-TGCGAAAGCCATTGGAGCAAC-3' (SEQ ID NO:34) was used; and (b) the PCR reaction was conducted by repeating 30 cycles of: denaturation at 94° C. for 1 min.; annealing at 53° C. for 1 min.; and DNA chain elongation at 72° C. for 30 sec.

(2) Preparation of Vector Incorporating Fusion DNA MWPsp-GH

A vector incorporating fusion DNA MWPsp-GH was prepared in the same manner as described in (5) of Example 9 except that: (a) template DNA was prepared by reacting a suitable amount of the DNA fragment MWPsp obtained in (1) of the present example with a suitable amount of the DNA fragment GH obtained in (3) of Example 9 at 16° C. for 30 min. using DNA ligation kit (Takara Shuzo, Co., Ltd.); (b) forward primer 5'-GTCGTTAACAGTGTATTGCT-3' (SEQ ID NO:6) and reverse primer 5'-CTAGAAGCCACAGCTGCCCT-3' (SEQ ID NO:45) were used; and (c) the PCR reaction was conducted by repeating 25 cycles of: denaturation at 94° C. for 1 min.; annealing at 53° C. for 1 min.; and DNA chain elongation at 72° C. for 1 min.

Example 11

Construction of Vectors Respectively Incorporating MWPsp-MWPmp1-, 2-, 3-, 4-, 5-, 6-, 7-, 8-, 9-, 10-, 11-, 12-, 14-, 30-TEV-G-GH (1) Preparation of DNA fragments MWPsp-MWPmp1-, 2-, 3-, 4-, 5-, 6-, 7-, 8-, 9-, 10-, 11-, 12-, 14-, 30

Blunt-ended DNA fragments MWPsp-MWPmp1, 2, 3, 4, 5, 6, 7, 8, 9, 10, 11, 12, 14, 30 were prepared in the same manner as described in (1) of Example 9 except that:

(a) the following primers were used as the reverse primers:

MWPmp1: 5'-TGCTGCGAAAGCCATTGG-3' (SEQ ID NO:24)

MWPmp2: 5'-TTCTGCTGCGAAAGCCAT-3' (SEQ ID NO:25)

MWPmp3: 5'-TTCTTCTGCTGCGAAAGC-3' (SEQ ID NO:26)

MWPmp4: 5'-TGCTTCTTCTGCTGCGAA-3' (SEQ ID NO:27)

MWPmp5: 5'-TGCTGCTTCTTCTGCTGC-3' (SEQ ID NO:28)

MWPmp6: 5'-AGTTGCTGCTTCTTCTGC-3' (SEQ ID NO:14)

MWPmp7: 5'-AGTAGTTGCTGCTTCTTC-3' (SEQ ID NO:29)

MWPmp8: 5'-TGTAGTAGTTGCTGCTTC-3' (SEQ ID NO:15)

(SEQ ID NO:16)

MWPmp9: 5'-AGCTGTAGTAGTTGCTGC-3' (SEQ ID NO:7)

MWPmp10: 5'-TGGAGCTGTAGTAGTTGCTGCTTCTTCTGC-3' (SEQ ID NO:17)

MWPmp11: 5'-TTTTGGAGCTGTAGTAGT-3' (SEQ ID NO:18)

MWPmp12: 5'-CATTTTTGGAGCTGTAGT-3' (SEQ ID NO:31)

MWPmp14: 5'-AGCGTCCATTTTTGGAGC-3' (SEQ ID NO:43)

MWPmp30: 5'-TGCTACCAGGCCAAGAGCTT-3';

and (b) the PCR reaction was conducted by repeating 30 cycles of: denaturation at 94° C. for 1 min.; annealing at 53° C. for 1 min.; and DNA chain elongation at 72° C. for 30 sec.

(2) Preparation of DNA Fragment TEV-G-GH

A blunt-ended DNA fragment TEV-G-GH was prepared in the same manner as described in (1) of Example 9 except that: (a) 10 ng of vector pG-GH incorporating the fusion DNA MWPsp-MWPmp20-TEV-G-GH obtained in (6) of Example 9 was used as template DNA; (b) forward primer 5'-GACTATGATATCCCGACCACT-3' (SEQ ID NO:60) and reverse primer 5'-CTAGAAGCCACAGCTGCCCT-3' (SEQ ID NO:45) were used; and (c) the PCR reaction was conducted by repeating 25 cycles of: denaturation at 94° C. for 1 min.; annealing at 55° C. for 1 min.; and DNA chain elongation at 72° C. for 30 sec.

The blunt-ended DNA fragment TEV-G-GH was then subjected to a phosphorylation reaction using T4 polynucleotide kinase (Nippon Gene) following the manufacturer's instruction, thereby obtaining phosphorylated DNA fragment TEV-G-GH.

(3) Preparation of Vectors Respectively Incorporating MWPsp-MWPmp1-, 2-, 3-, 4-, 5-, 6-, 7-, 8-, 9-, 10-, 11-, 12-, 14-, 30-TEV-G-GH Vectors respectively incorporating MWPsp-MWPmp1-, 2-, 3-, 4-, 5-, 6-, 7-, 8-, 9-, 10-, 11-, 12-, 14-, 30-TEV-G-GH were prepared in the same manner as described in (5) of Example 9 except that: (a) template DNA was prepared by reacting a suitable amount of the respective DNA fragments MWPsp-MWPmp1, 2, 3, 4, 5, 6, 7, 8, 9, 10, 11, 12, 14, 30 obtained in (1) of the present example with a suitable amount of the DNA fragment TEV-G-GH obtained in (2) of the present example at 16° C. for 30 min. using DNA ligation kit (Takara Shuzo, Co., Ltd.); (b) forward primer 5'-GTCGTTAACAGTGTATTGCT-3' (SEQ ID NO:6) and reverse primer 5'-CTAGAAGCCACAGCTGCCCT-3' (SEQ ID NO:45) were used; and (c) the PCR reaction was conducted by repeating 25 cycles of: denaturation at 94° C. for 1 min.; annealing at 53° C. for 1 min.; and DNA chain elongation at 72° C. for 1 min.

Example 12

Expression/Secretion of the Fusion Protein and Selective Cleavage of the Product (1) Amino Acid Sequence of the Fusion Products and Nucleotide Sequence Encoding the Same Among the fusion products obtained in Examples 9 to 11, the nucleotide sequence and amino acid sequence of the following product are representatively shown in SEQ ID NOS:52, 66, and FIG. 17.

MWPsp-MWPmp20-TEV-G-GH (SEQ ID NOS:52, 66)

(2) Expression/Secretion of the Fusion Products

The fusion proteins encoded by the fusion DNAs obtained in Examples 9 to 11 were expressed. FIG. 18 illustrates, as a representative example, a manner of introducing MWPsp-MWPmp20-TEV-G-GH into an expression vector.

Specifically, vectors incorporating the fusion DNAs obtained in Examples 9 to 11 were treated with restriction enzymes ApaLI and HindIII (when the fusion DNAs are inserted in a forward direction with respect to M13 primer for sequencing) or with ApaLI and KpnI (when the fusion DNAs are inserted in a reverse direction with respect to M13 primer for sequencing). Then, the restriction fragments were subjected to 0.8% agarose electrophoresis to cleave out DNA fragments with the fusion DNAs. A suitable amount of each of the thus-obtained fusion DNAs was reacted with a suitable amount of the *Bacillus brevis* expression vector pNU211R2L5 (JP-A-5-304962 and JP-A-7-170984) which had already been cleaved with ApaLI and HindIII (or KpnI when the fusion DNA is inserted in the reverse direction) at 16° C. for 30 min. using DNA ligation kit (Takara Shuzo, Co., Ltd.), thereby introducing each fusion DNA into respective expression vectors. These expression vectors were used to transform *Bacillus brevis* strain 47-5Q (FERM BP-1664, JP-A-60-58074 and JP-A-62-201589) according to a known method (Methods in Enzymol., 217:23, 1993) whereafter the resultant transformants were grown in respective T2 agar media [polypeptone (1%), meat extract (0.5%), yeast extract (0.2%), uracil (0.1 mg/ml), glucose (1%), erythromycin (10 μg/ml), agar (1.5%), pH 7].

The transformants were then respectively cultured in T2 media (removing agar from T2 agar media) at 37° C. for 1 day. Then, plasmid DNAs were purified from the media according to a known method (Molecular Cloning 2nd ed., A Laboratory Manual, Cold Spring Harbor Laboratory (1989)) and treated with ApaLI and HindIII (or KpnI) to confirm that the fusion DNAs were introduced into the transformants. For the transformants incorporating the fusion DNAs, expression/secretion of the fusion proteins encoded by the incorporated fusion DNAs were attempted. Specifically, cell suspensions obtained from the T2 media were respectively added to media [polypeptone (3%), yeast extract (0.4%), glucose (3%), $MgSO_4 7.H_2O$ (0.01%), $MnSO_4 4.H_2O$ (0.001%), erythromycin (10 μg/ml), pH 8] in a volume ratio of 1:1000, which were shake cultured in test tubes (2 ml/20-ml test tube) or Erlenmeyer flasks (50 ml/500-ml Erlenmeyer flask) at 30° C. for 4 days.

At the end of cultivation, the media were centrifuged at 15,000 rpm for 2 min. to obtain supernatants for analyzing proteins by electrophoresis according to a known method (Laemmli, U. K., Nature, 227, 680–685, 1970) Specifically, 18 μl of each supernatant was added to 2 μl of Buffer 1 [125 mM Tris-HCl (pH 6.8), 20% glycerol, 4% SDS, 10% 2-mercaptoethanol], boiled for 5 min., and then added to 4 μl of Buffer 2 [250 mM Tris-HCl (pH 6.5), 50% glycerol, 0.5% BPB]. The resultant supernatants were subjected to electrophoresis using commercially available 15/25% SDS polyacrylamide gel (Daiichi Chemicals, Co. Ltd., Japan) (electrophoresis buffer: 100 mM Tris, 100 mM Tricine, 0.1% SDS) in order to determine the presence of expression/secretion of the fusion proteins by subsequent Coomassie staining.

Figure 19:
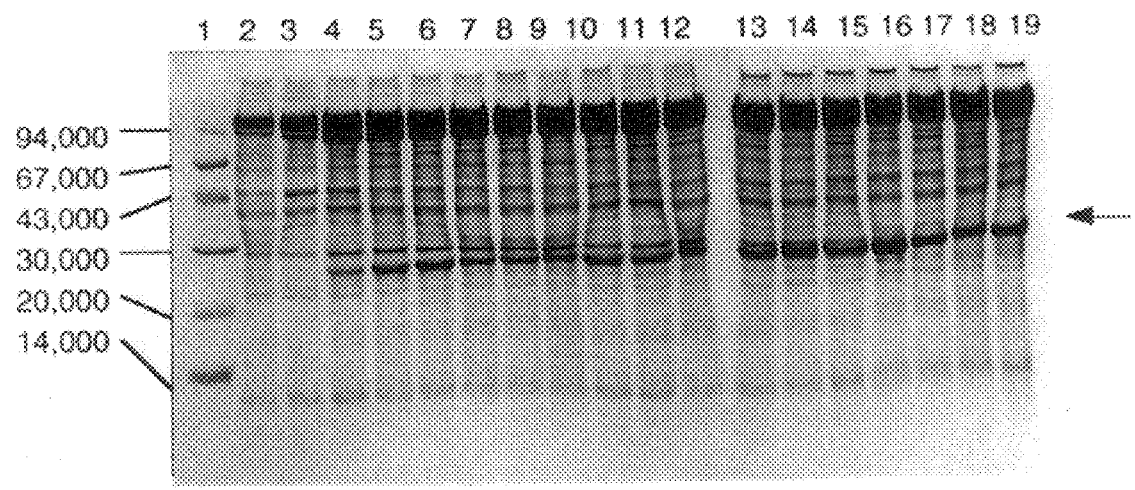
FIG. 19 is a photograph showing the results of electrophoresis of media containing human growth hormone produced by cultivation of the transformants: where the samples are marker proteins (lane 1), a negative control (transformed with plasmid pNU211R2L5 only; lane 2), transformant MWPsp-GH (lane 3), transformant MWPsp-TEV-G-GH (lane 4) and transformants MWPsp-MWPmp1-(lane 5), 2-(lane 6), 3-(lane 7), 4-(lane 8), 5-(lane 9), 6-(lane 10), 7-(lane 11), 8-(lane 12), 9-(lane 13), 10-(lane 14), 11-(lane 15), 12-(lane 16), 14-(lane 17), 20-(lane 18), 30(lane 19)-TEV-G-GH.

FIG. 19 shows the results of expression/secretion of: MWPsp-GH where MWP signal peptide is directly followed by a human growth hormone; MWPsp-TEV-G-GH where MWP signal peptide is directly followed by fusion product TEV-G-GH (i.e., combination of TEV protease-recognized sequence and mutant human growth hormone G-GH); and MWPsp-MWPmp1-, 2-, 3-, 4-, 5-, 6-, 7-, 8-, 9-, 10-, 1-, 12-, 14-, 20-, 30-TEV-G-GH proteins where MWP signal peptide is followed by fusion product TEV-G-GH via at least one amino acid residue of MWP protein from its N-terminus. The electrophoresis image of MWPsp-GH was similar to that of the expressed product of the vector pNU211R2L5 without exogenous polypeptide gene. Thus, MWPsp-GH did not have a clear band corresponding to growth hormone. On the other hand, the expression/secretion of fusion proteins were observed (as indicated by an arrow in FIG. 19) for MWPsp-TEV-G-GH and MWPsp-MWPmp1-, 2-, 3-, 4-, 5-, 6-, 7-, 8-, 9-, 10-, 11-, 12-, 14- 20-, 30-TEV-G-GH proteins. The expression levels of MWPsp-MWPmp1-, 2-, 3-, 4-, 5-, 6-, 7-, 8-, 9-, 10-, 11-, 12-, 14- 20-, 30-TEV-G-GH proteins were particularly higher compared with that of MWPsp-MWPmp1-TEV-G-GH.

Figure 20:
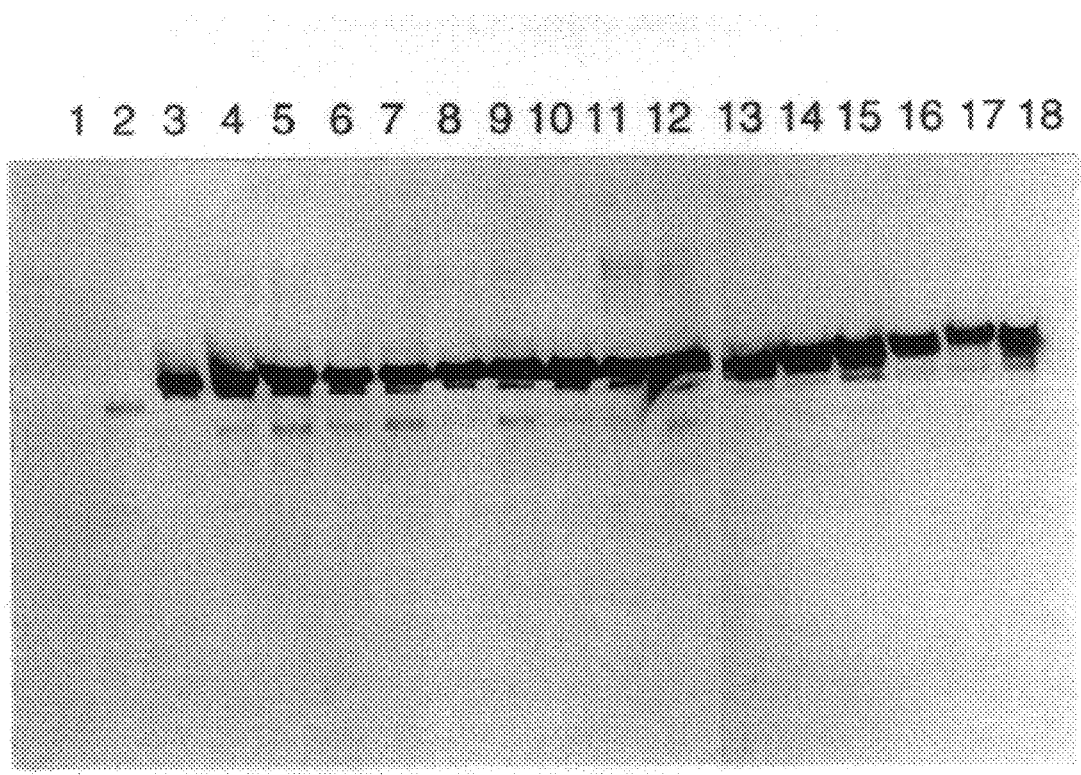
FIG. 20 is a photograph showing the results of Western blotting of human growth hormone produced by cultivation of the transformants: where the samples are a negative control (transformed with plasmid pNU211R2L5 only; lane 1), transformant MWPsp-GH (lane 2), transformant MWPsp-TEV-G-GH (lane 3), and transformants MWPsp-MWPmp1-(lane 4), 2-(lane 5), 3-(lane 6), 4-(lane 7), 5-(lane 8), 6-(lane 9), 7-(lane 10), 8-(lane 11), 9-(lane 12), 10-(lane 13), 11-(lane 14), 12-(lane 15), 14-(lane 16), 20-(lane 17), 30(lane 18)-TEV-G-GH.

(3) Identification of Human Growth Hormone GH and Mutant Human Growth Hormone G-GH Human growth hormone and mutant human growth hormone were immunologically identified using an antibody to human growth hormone (Western blotting method). The media of the respective transformants obtained in (2) of the present example were centrifuged at 15,000 rpm for 2 min. to obtain a supernatant of each medium. One μl of each of the supernatants were subjected to electrophoresis as described in (2) of the present example and then electrically blotted onto a nitrocellulose membrane according to a known method (Towbin, H. et al., 76, 4350–4354, 1979). The membrane was immersed in a solution of 5% skim milk in Buffer 3 [20 mM Tris-HCl (pH 7.4), 150 mM NaCl, 0.1% Tween 20] for 15 min. and then immersed in a rabbit anti-human growth hormone antibody (Biostride, Inc.) diluted 1:2,000 in Buffer 3, for 30 min. under shaking condition. The membrane was then washed with Buffer 3, for 10 min. 3 times under shaking condition and immersed in a peroxidase-labeled anti-rabbit IgG antibody (E-Y Laboratories) diluted 1:2000 in Buffer 3 for 30 min. under shaking condition. After the immersion, the membrane was washed with Buffer 3 for 10 min. 3 times while shaking, in order to determine the presence of GH and G-GH using ECL detection kit (Amersham International plc) according to the manufacturers' instruction. As shown in FIG. 20, signals were detected for all fusion products other than pNU211R2L5 without any exogenous polypeptide gene, i.e., MWPsp-GH, MWPsp-TEV-G-GH, MWPsp-MWPmp1-, 2-, 3-, 4-, 5-, 6-, 7-, 8-, 9-, 10-, 11-, 12-, 14-, 20-, 30-TEV-G-GH. For MWPsp-GH where MWP signal peptide is directly followed by human growth hormone, no band corresponding to human growth hormone was detected by Coomassie staining following SDS-PAGE whereas a signal was detected by the Western blotting method. Considering the fact that Western blotting method is much sensitive than Comassie staining, when human growth hormone was preceded by MWP signal peptide, MWPsp-GH was capable of expression/secretion but with a low expression level.

(4) Cleavage of Mutant Human Growth Hormone

Figure 21:
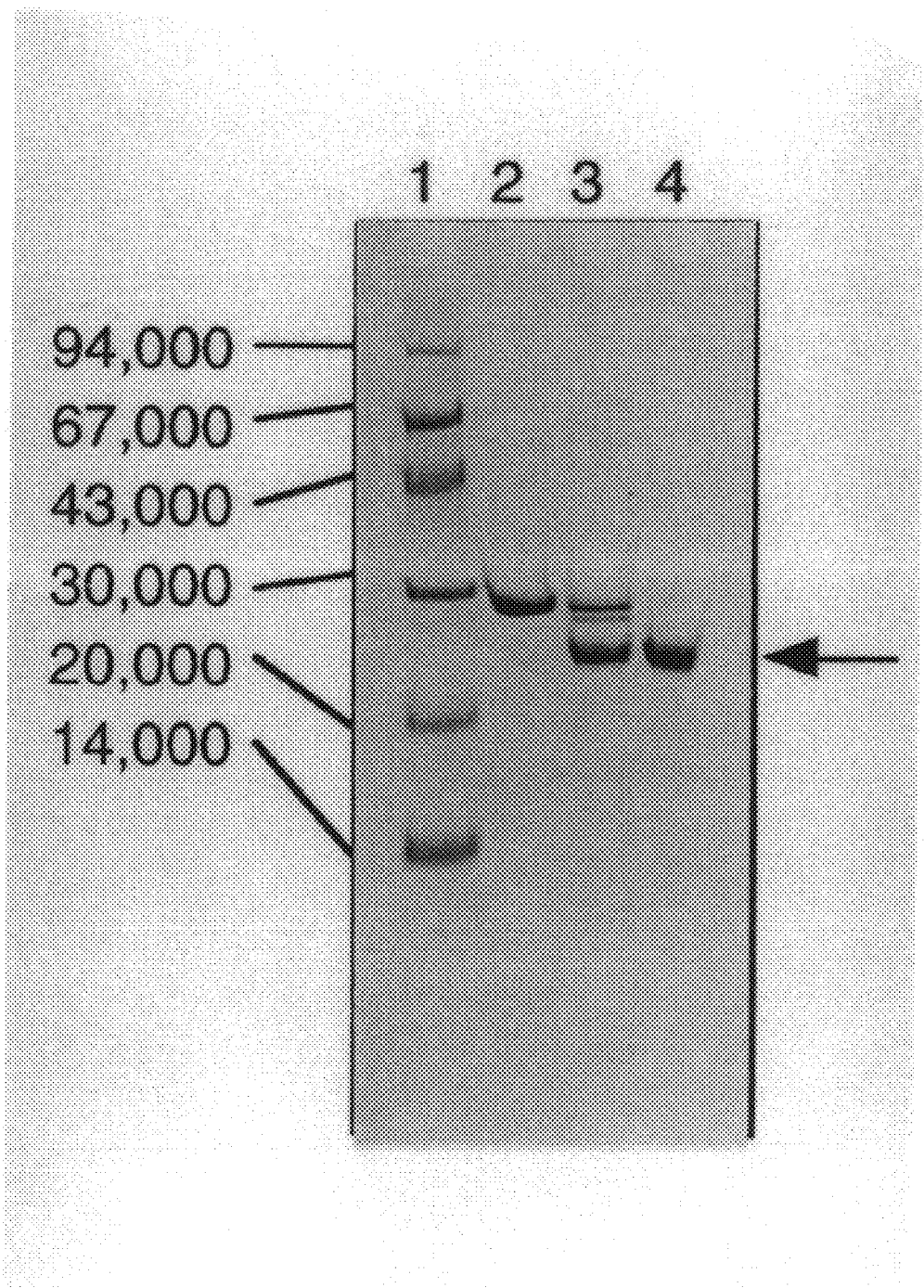
FIG. 21 is a photograph showing the results of electrophoresis of separated and purified fusion protein MWPmp20-TEV-G-GH and mutant human growth hormone G-GH cleaved therefrom via TEV protease treatment: where the samples are marker proteins (lane 1); the separated and purified fusion protein MWPmp20-TEV-G-GH (5 µg, lane 2); the mutant human growth hormone G-GH cleaved from the fusion protein via TEV protease treatment (5 µg, lane 3); and human growth hormone (Biogenesis) (5 µg, lane 4).
Figure 22:
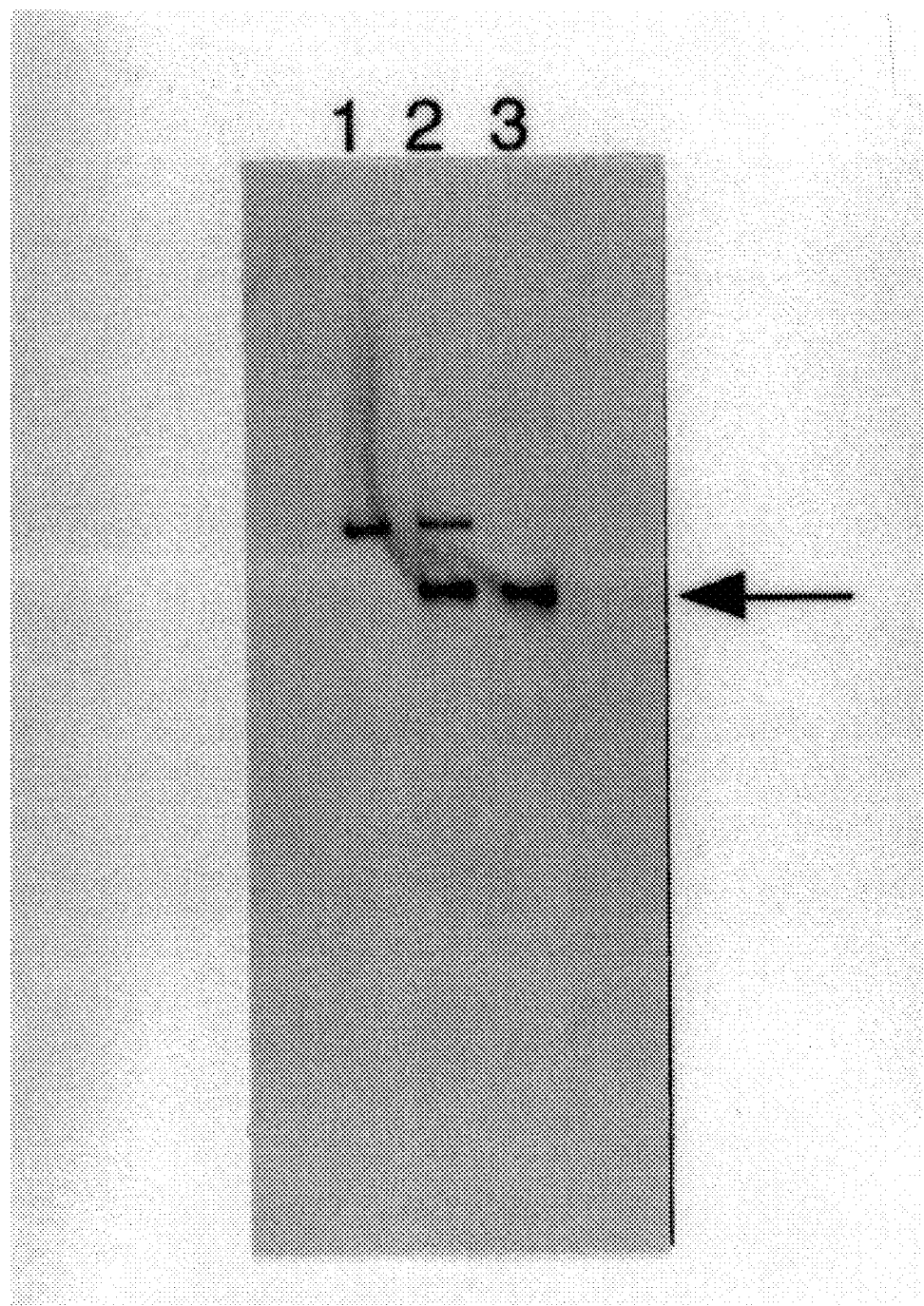
FIG. 22 is a photograph showing the results of Western blotting of separated and purified fusion protein MWPmp20-TEV-G-GH and mutant human growth hormone G-GH cleaved therefrom via TEV protease treatment: where the samples are the separated and purified fusion protein MWPmp20-TEV-G-GH (0.1 µg, lane 1); the mutant human growth hormone G-GH cleaved from the fusion protein via TEV protease treatment (0.1 µg, lane 2); and human growth hormone (Biogenesis) (0.1 µg, lane 3).

A transformant containing an expression vector incorporating fusion DNA MWPsp-MWPmp20-TEV-G-GH was cultured overnight in a medium. The suspension of the medium (volume ratio 1:1000) was added to ten 500-ml Erlenmeyer flasks each containing 50 ml of the same medium used for expression in (2) of Example 4 and cultured at 30° C. for 4 days. The obtained media were each centrifuged at 10,000 rpm at 4° C. for 20 min., added with EDTA to a final concentration of 5 mM, and precipitated by adding ammonium sulfate to 60% saturation. After another centrifugation at 10,000 rpm for 20 min., the pellet was dissolved in a suitable amount of Tris-hydrochloric acid buffer (20 mM Tris-HCl, 1 mM EDTA, pH 8) and applied to a Sephadex G-25 (Pharmacia) column for a buffer exchange. The resultant was applied and adsorbed to an anion-exchange resin (Pharmacia, QXL) column equilibrated with Buffer A [20 mM Tris-HCl, 1 mM EDTA, 1 M Urea, 20% propanol, pH 8] and subjected to gradient elution with Buffer B (Buffer A +1 M NaCl). Fractions positive to an anti-human growth hormone antibody that were eluted at 220–300 mM NaCl were condensed with Ultrafree (Millipore Corp., UFV2BCC40) while replacing with Buffer C [0.1% TFA, 10% acetonitrile], and applied to an RPC column (Pharmacia) for a reversed-phase chromatography. As a result of subsequent gradient elution with Buffer D [0.1% TFA, 60% acetonitrile], the target fusion protein MWPmp20-TEV-G-GH was eluted at 45–50% acetonitrile. The thus-obtained fusion protein was dialyzed against 2 mM Tris-HCl (pH 8) and used in a TEV protease treatment. Five μg of the fusion protein was treated with TEV protease (GIBCO BRL, 5 U) according to the manufacturer's instruction to cleave out mutant human growth hormone G-GH. FIGS. 21 and 22 are images of SDS-PAGE and Western blotting respectively showing the cleavage results. The SDS-PAGE and Western blotting were performed in the same manner as described in (2) and (3) of the present example. Referring to FIGS. 21 and 22, the mutant human growth hormone G-GH with extra Gly at the N-terminus was cleaved at the same position (as indicated by an arrow) as the commercially available human growth hormone (positive control).

Expressions of other polypeptides hNGF, mLIF, bSCF and hPDGF-B were also attempted in the same manner as in the Examples. No secretion was observed when the number of amino acids of MWP from the N-terminus was 10, 40 or 100. This suggests that a chance of secretion through fusion with at least one amino acid of MWP from its N-terminus possibly depends on the type of exogenous polypeptide used.

The present invention enables high expression/secretion through the novel fusion with an exogenous protein, and also enables production of a natural protein through chemical or enzymatic selective cleavage.

All publications including patent applications cited herein are incorporated herein by reference in their entirety.

The following are information on sequences of SEQ ID NOS:48–52, 62–66 described herein:

```
SEQ ID NO:48:
gtcgttaaca gtgtattggc tagtgcactc gcacttactg ttgctccaat ggctttcgca   60
gcagaagaag cagcaactac tacagctcca catcatcatc atcatcacgg ttctccagta  120
ccttctggaa tgtttgtgaa ccaacacctg tgcggctcac acctggtgga agctctctac  180
ctagtgtgcg gggaaagagg cttcttctac acacccaaga cccgccggga ggcagaggac  240
ctgcaggtgg ggcaggtgga gctgggcggg ggccctggtg caggcagcct gcagcccttg  300
gccctggagg ggtccctgca gaagcgtggc attgtggaac aatgctgtac cagcatctgc  360
tccctctacc agctggagaa ctactgcaac                                   390

SEQ ID NO:49:
gtcgttaaca gtgtattggc tagtgcactc gcacttactg ttgctccaat ggctttcgca   60
gcagaagaag cagcaactac tacagctcca atgtttgtga accaacacct gtgcggctca  120
cacctggtgg aagctctcta cctagtgtgc ggggaaagag gcttcttcta cacacccaag  180
acccgccggg aggcagagga cctgcaggtg gggcaggtgg agctgggcgg gggccctggt  240
gcaggcagcc tgcagccctt ggccctggag gggtccctgc agaagcgtgg cattgtggaa  300
caatgctgta ccagcatctg ctccctctac cagctggaga actactgcaa c           351

SEQ ID NO:50:
gtcgttaaca gtgtattggc tagtgcactc gcacttactg ttgctccaat ggctttcgca   60
gcagaagaag cagcaactac tacagctcca aaaatggacg ctgatatgga aaaaccgta  120 catcatcatc atcatcacaa ctctgactcc gaatgcccgc tgtctcacga cggttattgc  180
ctgcatgatg gtgtttgtat gtatatcgaa gctctggaca aatatgcttg caactgtgtt  240
gttggttaca tcggtgagcg ttgccagtat cgcgacctga atggtgggga actgcgtgac  300
tatgatatcc cgaccactga aaacctgtac ttccaatctg ctaactcaaa cccggctatg  360
gcaccccgag aacgcaaagc tggctgcaag aatttcttct ggaagacttt cacatcctgt  420

SEQ ID NO:51:
gtcgttaaca gtgtattggc tagtgcactc gcacttactg ttgctccaat ggctttcgca   60
gcagaagaag cagcaactac tacagctcca aaaatggacg ctgatatgga aaaaccgta  120 catcatcatc atcatcacgg ttctccagta ccttctggat tcctggaaca cagccaaggt  180
```

```
actttcacat ccgactactc taaatatctg gattcccgtc gcgctcaaga tttcgttcaa   240
tggCtgatga acact                                                    255
SEQ ID NO:52:
gtcgttaaca gtgtattggc tagtgcactc gcacttactg ttgctccaat ggctttcgca    60
gcagaagaag cagcaactac tacagctcca aaaatggacg ctgatatgga aaaaccgta   120
gactatgata tcccgaccac tgaaaacctg tacttccaag gtttcccaac cattcccta   180
tccaggcttt ttgacaacgc tatgctccgc gcccatcgtc tgcaccagct ggcctttgac   240
acctaccagg agtttgaaga agcctatatc caaaggaac agaagtattc attcctgcag   300
aacccccaga cctccctctg tttctcagag tctattccga caccctccaa cagggaggaa   360
acacaacaga aatccaacct agagctgctc cgcatctccc tgctgctcat ccagtcgtgg   420
ctggagcccg tgcagttcct caggagtgtc ttcgccaaca gcctggtgta cggcgcctct   480
gacagcaacg tctatgacct cctaaaggac ctagaggaag catccaaac gctgatgggg   540
aggctggaag atggcagccc ccggactggg cagatcttca agcagaccta cagcaagttc   600
gacacaaact cacacaacga tgacgcacta ctcaagaact acgggctgct ctactgcttc   660
aggaaggaca tggacaaggt cgagacattc ctgcgcatcg tgcagtgccg ctctgtggag   720
ggcagctgtg gcttc                                                    735

SEQ NO ID: 62:
Val Val Asn Ser Val Leu Ala Ser Ala Leu Ala Leu Thr Val Ala Pro
  1               5                  10                  15
Met Ala Phe Ala Ala Glu Glu Ala Ala Thr Thr Thr Ala Pro His His
              20                  25                  30
His His His His Gly Ser Pro Val Pro Ser Gly Met Phe Val Asn Gln
          35                  40                  45
His Leu Cys Gly Ser His Leu Val Glu Ala Leu Tyr Leu Val Cys Gly
      50                  55                  60
Glu Arg Gly Phe Phe Tyr Thr Pro Lys Thr Arg Arg Glu Ala Glu Asp
 65                  70                  75                  80
Leu Gln Val Gly Gln Val Glu Leu Gly Gly Gly Pro Gly Ala Gly Ser
                  85                  90                  95
Leu Gln Pro Leu Ala Leu Glu Gly Ser Leu Gln Lys Arg Gly Ile Val
             100                 105                 110
Glu Gln Cys Cys Thr Ser Ile Cys Ser Leu Tyr Gln Leu Glu Asn Tyr
         115                 120                 125
Cys Asn
    130

SEQ ID NO:63:
Val Val Asn Ser Val Leu Ala Ser Ala Leu Ala Leu Thr Val Ala Pro
  1               5                  10                  15
Met Ala Phe Ala Ala Glu Glu Ala Ala Thr Thr Thr Ala Pro Met Phe
              20                  25                  30
Val Asn Gln His Leu Cys Gly Ser His Leu Val Glu Ala Leu Tyr Leu
          35                  40                  45
Val Cys Gly Glu Arg Gly Phe Phe Tyr Thr Pro Lys Thr Arg Arg Glu
      50                  55                  60
Ala Glu Asp Leu Gln Val Gly Gln Val Glu Leu Gly Gly Gly Pro Gly
 65                  70                  75                  80
Ala Gly Ser Leu Gln Pro Leu Ala Leu Glu Gly Ser Leu Gln Lys Arg
                  85                  90                  95
Gly Ile Val Glu Gln Cys Cys Thr Ser Ile Cys Ser Leu Tyr Gln Leu
             100                 105                 110
Glu Asn Tyr Cys Asn
         115

SEQ ID NO:64:
Val Val Asn Ser Val Leu Ala Ser Ala Leu Ala Leu Thr Val Ala Pro
  1               5                  10                  15
Met Ala Phe Ala Ala Glu Glu Ala Ala Thr Thr Thr Ala Pro Lys Met
              20                  25                  30
Asp Ala Asp Met Glu Lys Thr Val His His His His His His Asn Ser
          35                  40                  45
Asp Ser Glu Cys Pro Leu Ser His Asp Gly Tyr Cys Leu His Asp Gly
      50                  55                  60
```

-continued

```
SEQ ID NO:64 (continued):
Val Cys Met Tyr Ile Glu Ala Leu Asp Lys Tyr Ala Cys Asn Cys Val
 65                  70                  75                  80
Val Gly Tyr Ile Gly Glu Arg Cys Gln Tyr Arg Asp Leu Lys Trp Trp
                 85                  90                  95
Glu Leu Arg Asp Tyr Asp Ile Pro Thr Thr Glu Asn Leu Tyr Phe Gln
            100                 105                 110
Ser Ala Asn Ser Asn Pro Ala Met Ala Pro Arg Glu Arg Lys Ala Gly
        115                 120                 125
Cys Lys Asn Phe Phe Trp Lys Thr Phe Thr Ser Cys
130                 135                 140

SEQ ID NO:65:
Val Val Asn Ser Val Leu Ala Ser Ala Leu Ala Leu Thr Val Ala Pro
  1               5                  10                  15
Met Ala Phe Ala Ala Glu Glu Ala Ala Thr Thr Thr Ala Pro Lys Met
                 20                  25                  30
Asp Ala Asp Met Glu Lys Thr Val His His His His His Gly Ser
             35                  40                  45
Pro Val Pro Ser Gly Phe Leu Glu His Ser Gln Gly Thr Phe Thr Ser
         50                  55                  60
Asp Tyr Ser Lys Tyr Leu Asp Ser Arg Arg Ala Gln Asp Phe Val Gln
 65                  70                  75                  80
Trp Leu Met Asn Thr
                 85

SEQ ID NO:66:
Val Val Asn Ser Val Leu Ala Ser Ala Leu Ala Leu Thr Val Ala Pro
  1               5                  10                  15
Met Ala Phe Ala Ala Glu Glu Ala Ala Thr Thr Thr Ala Pro Lys Met
                 20                  25                  30
Asp Ala Asp Met Glu Lys Thr Val Asp Tyr Asp Ile Pro Thr Thr Glu
             35                  40                  45
Asn Leu Tyr Phe Gln Gly Phe Pro Thr Ile Pro Leu Ser Arg Leu Phe
         50                  55                  60
Asp Asn Ala Met Leu Arg Ala His Arg Leu His Gln Leu Ala Phe Asp
 65                  70                  75                  80
Thr Tyr Gln Glu Phe Glu Glu Ala Tyr Ile Pro Lys Glu Gln Lys Tyr
                 85                  90                  95
Ser Phe Leu Gln Asn Pro Gln Thr Ser Leu Cys Phe Ser Glu Ser Ile
            100                 105                 110
Pro Thr Pro Ser Asn Arg Glu Glu Thr Gln Gln Lys Ser Asn Leu Glu
        115                 120                 125
Leu Leu Arg Ile Ser Leu Leu Leu Ile Gln Ser Trp Leu Glu Pro Val
130                 135                 140
Gln Phe Leu Arg Ser Val Phe Ala Asn Ser Leu Val Tyr Gly Ala Ser
145                 150                 155                 160
Asp Ser Asn Val Tyr Asp Leu Leu Lys Asp Leu Glu Glu Gly Ile Gln
                165                 170                 175
Thr Leu Met Gly Arg Leu Glu Asp Gly Ser Pro Arg Thr Gly Gln Ile
            180                 185                 190
Phe Lys Gln Thr Tyr Ser Lys Phe Asp Thr Asn Ser His Asn Asp Asp
        195                 200                 205
Ala Leu Leu Lys Asn Tyr Gly Leu Leu Tyr Cys Phe Arg Lys Asp Met
    210                 215                 220
Asp Lys Val Glu Thr Phe Leu Arg Ile Val Gln Cys Arg Ser Val Glu
225                 230                 235                 240
Gly Ser Cys Gly Phe
                245
```

What is claimed is:

1. An isolated DNA, which is capable of producing an exogenous polypeptide in *Bacillus brevis*, comprising a nucleotide sequence linked to the 3' end of a nucleic acid sequence of a Bacillus promoter region and encoding a fusion protein that comprises: a first, a second and a third sequence being linearly linked, wherein said first sequence consists of a sequence of n amino acid residues beginning at the N-terminus of a mature cell wall protein of a Bacillus bacterium, wherein n is 6, 7, 8, 10, 11, 12, 15, 17, 20 or 50 when the exogenous polypeptide is human proinsulin, 20 when the exogenous polypeptide is human glucagon, and 1–12, 14, 20 or 30 when the exogenous polypeptide is a mutant human growth hormone, the second sequence consists of one or more amino acid residues for chemically or enzymatically cleaving said third sequence from said first sequence, said second sequence not being found in the first sequence or the third sequence, and the third sequence comprises an exogenous polypeptide sequence selected from the group consisting of human proinsulin, human glucagon, and a mutant human growth hormone with glycine or serine at the N-terminus and whereby said third sequence is capable of being chemically or enzymatically cleaved from said first sequence only at said second sequence.

2. The DNA of claim 1, wherein said fusion protein further comprises a Bacillus cell wall protein signal peptide sequence at the N-terminus.

3. The DNA of claim 2, wherein said fusion protein further comprises a sequence consisting of amino acid residues used as a tag for separation and purification.

4. The DNA of claim 2, wherein said fusion protein further comprises a sequence consisting of amino acid residues for use as a linker.

5. The DNA of claim 2, wherein said Bacillus bacterium is *Bacillus brevis*.

6. The DNA of claim 1, wherein the second sequence for chemically or enzymatically cleaving said third sequence from said first sequence is methionine.

7. The DNA of claim 1, wherein the second sequence for chemically or enzymatically cleaving said third sequence from said first sequence comprises a sequence capable of being cleaved with a protease.

8. The DNA of claim 1, wherein said first sequence consists of 6, 7, 8, 10, 11, 12, 15, 17, 20 or 50 amino acid residues from the N-terminus of a middle wall protein which is a cell wall protein; said second sequence comprises a methionine residue for chemically cleaving said third sequence from said first sequence; and said third sequence containing no methionine within its amino acid sequence and being human proinsulin; and said fusion protein further comprises a fourth sequence consisting of six histidine residues as a tag for separation and purification, and a fifth sequence comprising an amino acid sequence comprising SEQ ID NO: 1 as a linker, said fourth and fifth sequences being linked linearly to one another in order between said first and second sequences.

9. The DNA of claim 8, wherein said fusion protein further comprises a middle wall protein signal peptide sequence at the N-terminus.

10. The DNA of claim 1, wherein said first sequence consists of twenty amino acid residues from the N-terminus of a middle wall protein which is a cell wall protein; said second sequence comprises an amino acid sequence of Phe Leu Glu for enzymatically cleaving said third sequence from said first sequence with V8 protease; and said third sequence comprises a polypeptide sequence containing no glutamic acid in its amino acid sequence and being human glucagons; and said fusion protein further comprises a fourth sequence comprising six histidine residues as a tag for separation and purification, and a fifth sequence comprising an amino acid sequence of SEQ ID NO: 1 as a linker; said fourth and fifth sequences being linked linearly to one another in order between said first and second sequences.

11. The DNA of claim 10, wherein said fusion protein further comprises a middle wall protein signal peptide sequence at the N-terminus.

12. The DNA of claim 1, wherein said first sequence comprises a signal peptide sequence for a middle wall protein which is a cell wall protein;
said second sequence of SEQ ID NO: 2 required for enzymatically cleaving said third sequence from said first sequence containing no TEV protease recognition sequence in its amino acid sequence and being a mutant human growth hormone having a glycine or a serine at the N-terminus; and said fusion protein further comprises a fourth sequence comprising a sequence of one or more an amino acid residues from the N-terminus of the MWP protein, said fourth sequence being linked linearly in order between said first and second sequences.

13. The DNA of claim 12, wherein said sequence of one or more amino acid residues from the N-terminus of the MWP protein comprises the N-terminal 1–12, 14, 20 or 30 amino acid residues.

14. An isolated DNA, which is capable of producing a human somatostatin 28 polypeptide in Bacillus brevis, comprising a nucleotide sequence encoding a fusion protein, wherein the fusion protein comprises a first, a second, a third and a fourth sequence being linearly linked in order, wherein the first sequence consists of 10 or 20 amino acid residues from the N-terminus of a mature cell wall protein of a Bacillus bacterium; the second sequence comprises human epidermal growth factor as a linker; the third sequence consists of amino acid residues for enzymatically cleaving the fourth sequence from the first sequence; and a fourth sequence of human somatostatin 28 polypeptide, and wherein said nucleotide sequence is linked to the 3' end of a nucleic acid sequence comprising a Bacillus promoter region.

15. The DNA of claim 14, wherein said fusion protein further comprises a middle wall protein signal peptide sequence at the N-terminus.

16. The DNA of claim 14, wherein said fusion protein further comprises a sequence consisting of amino acid residues used as a tag for separation and purification.

17. The DNA of claim 14, wherein said Bacillus bacterium is Bacillus brevis.

18. The DNA of claim 14, wherein the third sequence consisting of amino acid residues for enzymatically cleaving said fourth sequence comprises a sequence capable of being cleaved with a protease.

19. The DNA of claim 14, wherein said first sequence comprises a sequence consisting of 10 or 20 amino acid residues from the N-terminus of a middle wall protein which is a cell wall protein; said third sequence comprises an amino acid sequence of SEQ ID No: 2 for enzymatically cleaving said fourth sequence with TEV protease; and said fourth sequence containing no TEV protease recognition sequence in its amino acid sequence and contains glycine or serine at the N-terminus; and said fusion protein further comprises a fifth sequence consisting of six histidine residues as a tag for separation and purification, said fifth sequence being linked linearly in order between said first and second sequences.

20. A vector comprising the DNA according to claim 2.

21. A bacterium Bacillus brevis transformed with the vector according to claim 20.

22. A vector comprising the DNA according to claim 14.

23. A bacterium Bacillus brevis transformed with the vector according to claim 22.

24. The DNA of claim 1, wherein said fusion protein further comprises a sequence consisting of amino acid residues used as a tag for separation and purification, wherein said tag is $His_6$.

* * * * *

UNITED STATES PATENT AND TRADEMARK OFFICE
CERTIFICATE OF CORRECTION

PATENT NO.     : 6,506,595 B2
DATED          : January 14, 2003
INVENTOR(S)    : Sato et al.

It is certified that error appears in the above-identified patent and that said Letters Patent is hereby corrected as shown below:

<u>Title page,</u>
Item [73], Assignee, please replace "Shigeo Udaka" with -- Shigezo Udaka --

Signed and Sealed this

Twenty-fourth Day of June, 2003

JAMES E. ROGAN
*Director of the United States Patent and Trademark Office*